(12) United States Patent
Mondy

(10) Patent No.: US 11,528,902 B2
(45) Date of Patent: Dec. 20, 2022

(54) METHOD AND APPARATUS FOR KEEPING ARTIFICIALLY CREATED TISSUES ALIVE

(71) Applicant: William Lafayette Mondy, Tampa, FL (US)

(72) Inventor: William Lafayette Mondy, Temple Terrace, FL (US)

(73) Assignee: William L. Mondy, Temple Terrace, FL (US)

( * ) Notice: Subject to any disclaimer, the term of this patent is extended or adjusted under 35 U.S.C. 154(b) by 0 days.

(21) Appl. No.: 17/339,970

(22) Filed: Jun. 5, 2021

(65) Prior Publication Data

US 2021/0345604 A1 Nov. 11, 2021

Related U.S. Application Data

(62) Division of application No. 15/359,487, filed on Nov. 22, 2016, now Pat. No. 11,051,509.

(51) Int. Cl.
| | | |
|---|---|---|
| *A01N 1/02* | (2006.01) |
| *C12M 1/00* | (2006.01) |
| *C12M 1/34* | (2006.01) |
| *C12M 3/00* | (2006.01) |
| *C12M 1/36* | (2006.01) |
| *C12M 1/12* | (2006.01) |
| *G06F 30/00* | (2020.01) |

(52) U.S. Cl.
CPC ............ *A01N 1/0242* (2013.01); *C12M 21/08* (2013.01); *C12M 23/02* (2013.01); *C12M 25/14* (2013.01); *C12M 29/00* (2013.01); *C12M 41/36* (2013.01); *C12M 41/48* (2013.01); *G06F 30/00* (2020.01)

(58) Field of Classification Search
CPC ..... A01N 1/0242; C12M 21/08; C12M 23/02; C12M 25/14; C12M 29/00; C12M 41/36; C12M 41/48; G06F 30/00
See application file for complete search history.

(56) References Cited

U.S. PATENT DOCUMENTS 11,051,509 B2 * 7/2021 Mondy .................. C12M 41/36

* cited by examiner

*Primary Examiner* — Blaine Lankford

(57) ABSTRACT

A device to aid in the production and regeneration of tissues and organs, standing alone, or on or inside of the human body, with a method of fabrication of tissues and organs and use of the device.

6 Claims, 14 Drawing Sheets

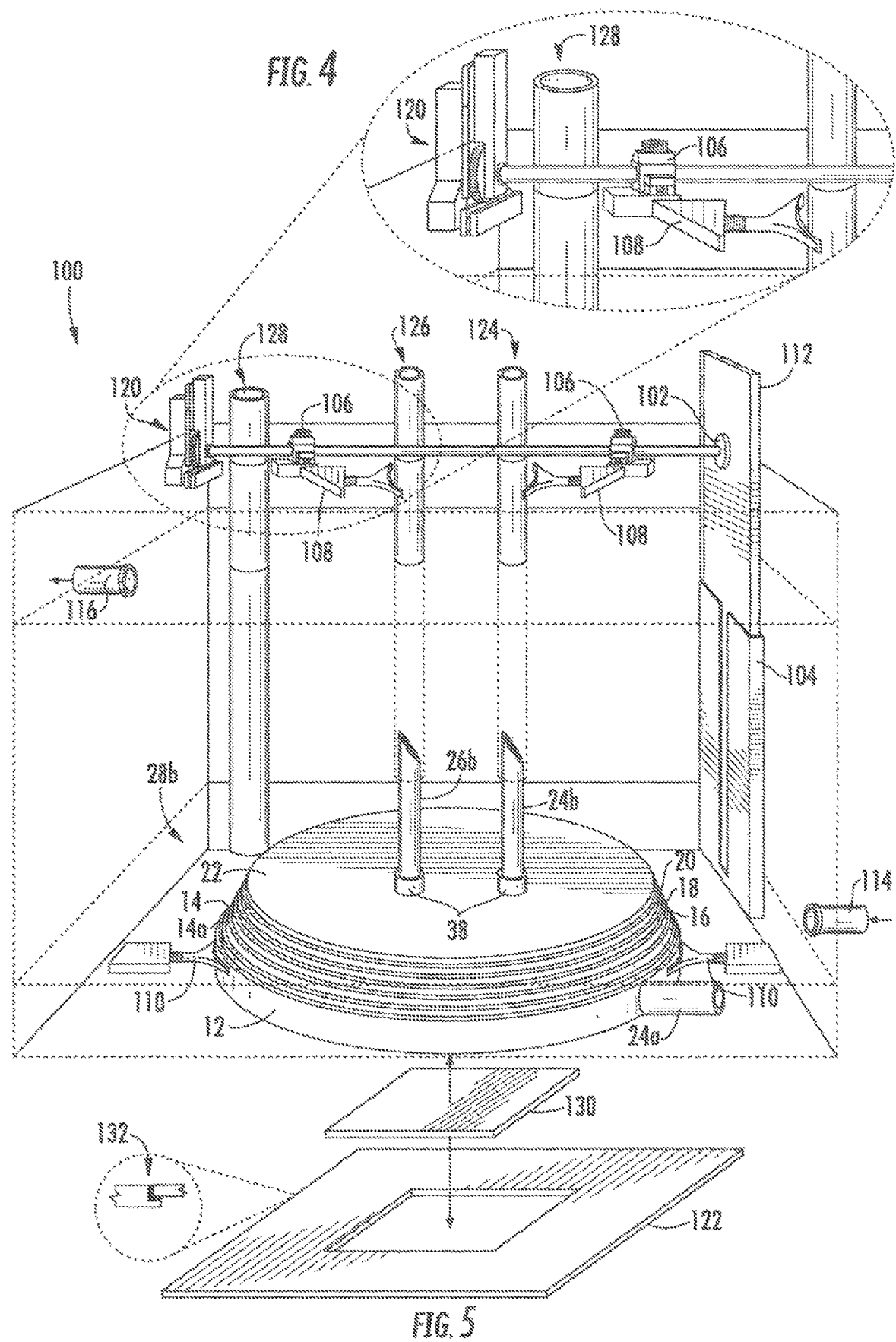

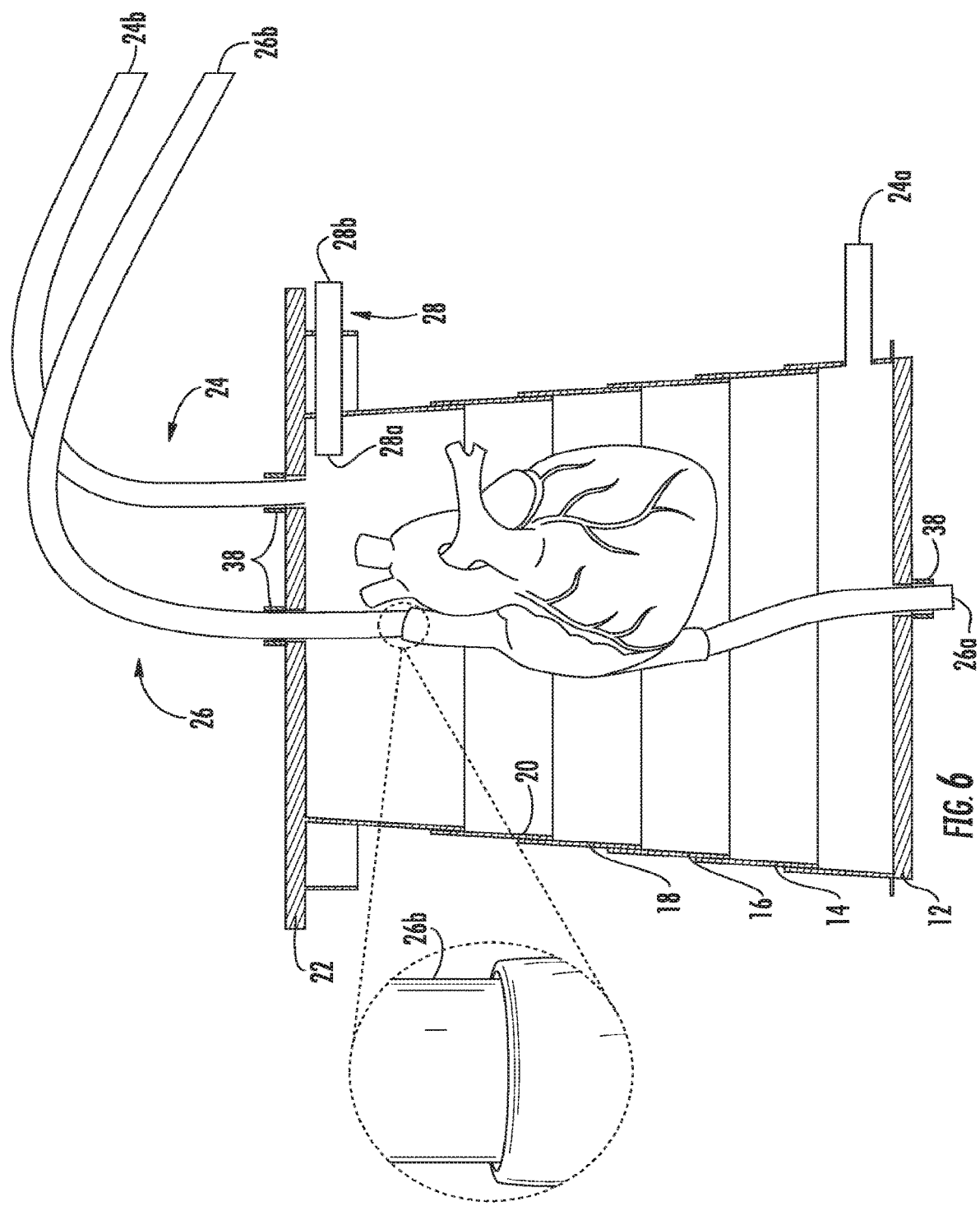

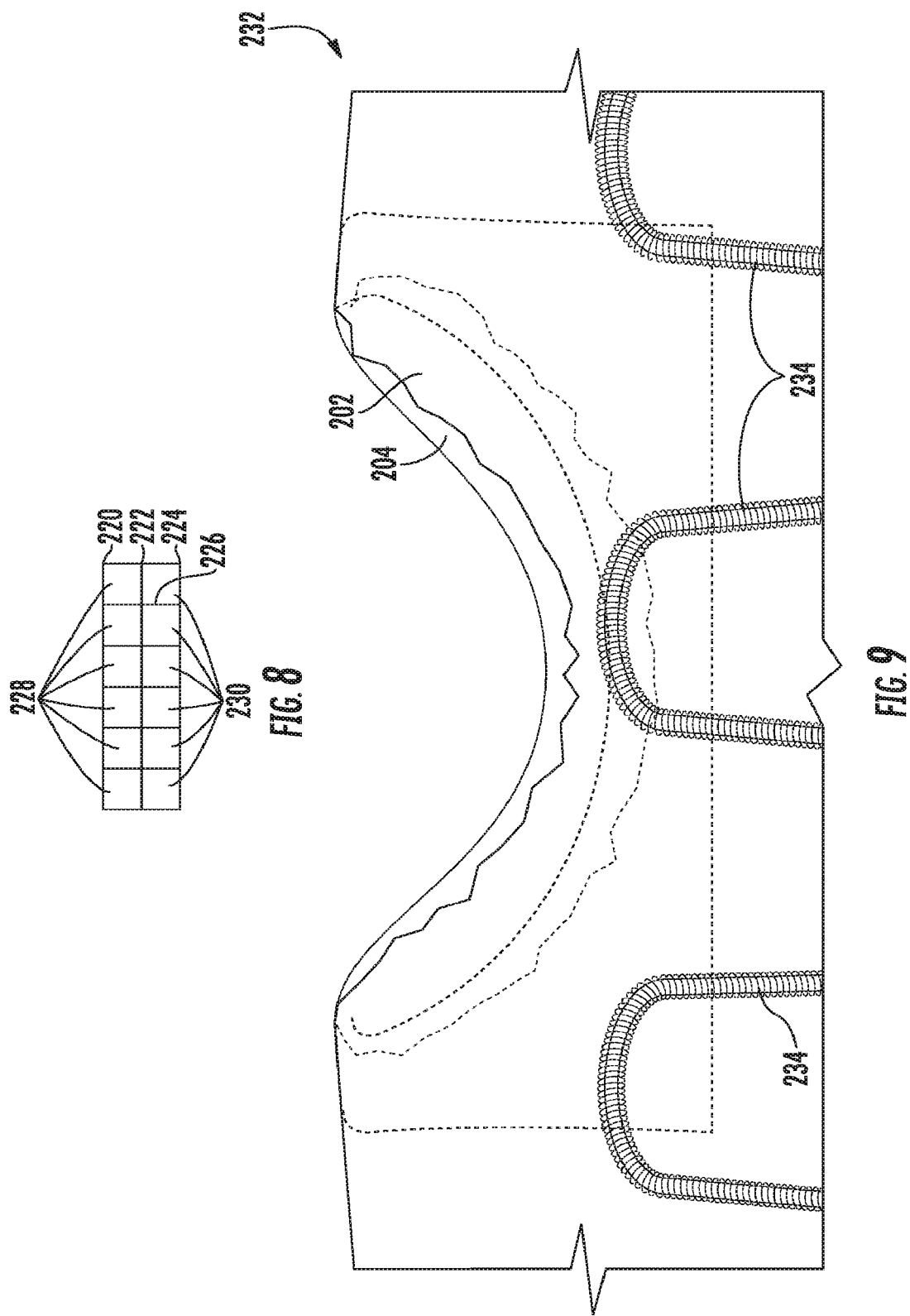

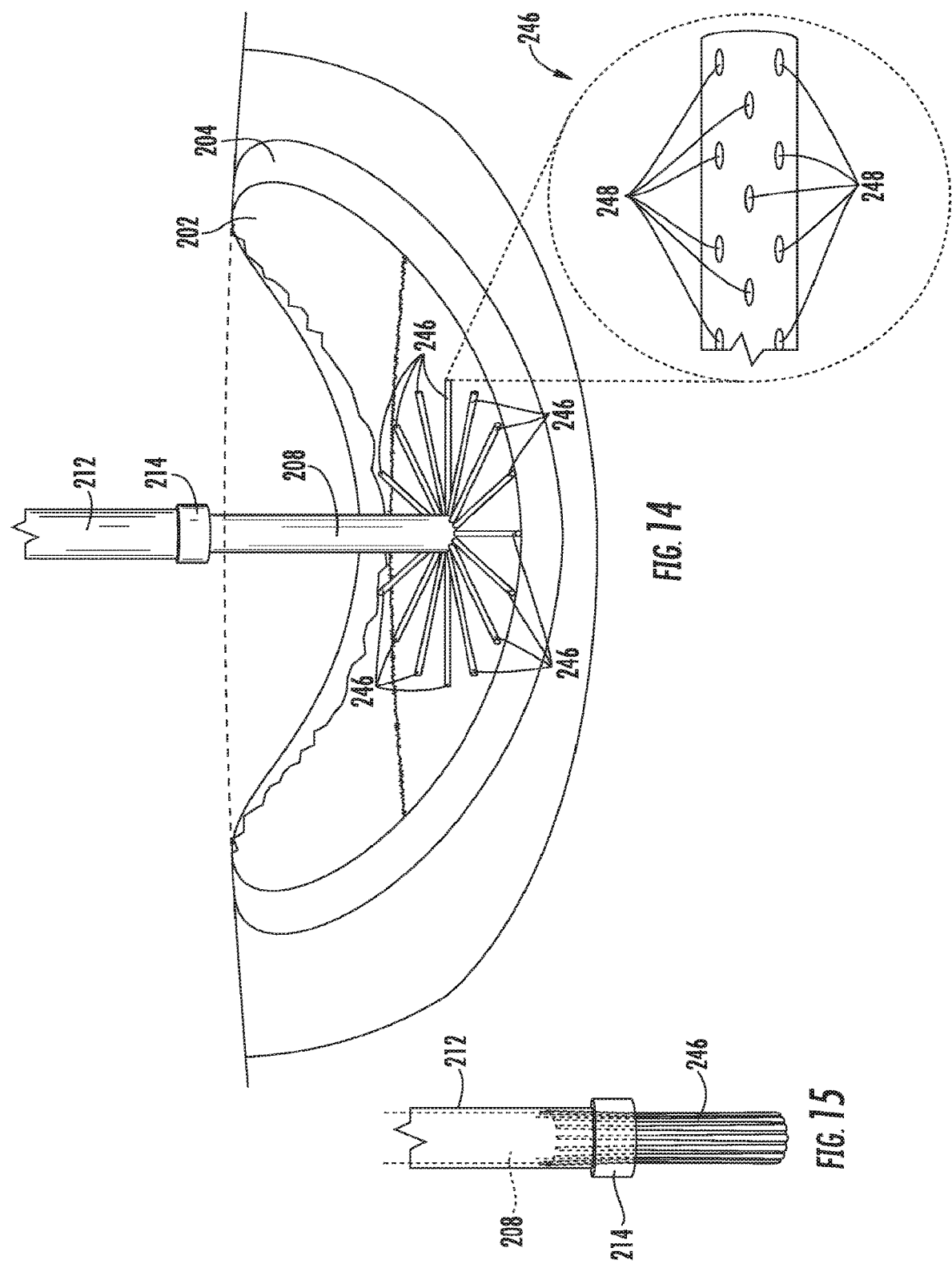

METHOD AND APPARATUS FOR KEEPING ARTIFICIALLY CREATED TISSUES ALIVE

CROSS REFERENCE TO RELATED APPLICATIONS

This is a division of patent application Ser. No. 15/359,487. Filed Nov. 22, 2016 now pending

FEDERALLY SPONSORED RESEARCH

Not applicable.

NAMES OF PARTIES TO A JOINT RESEARCH AGREEMENT

Not applicable.

INCORPORATE BY REFERENCE CD OF SEQUENCE LISTING OR PROGRAM LISTING

Not applicable.

PRIOR DISCLOSURES BY INVENTOR OR JOINT INVENTOR

Not applicable.

BACKGROUND

1. Field of the Invention

Generally, the invention relates to biomedical research and development, and biomedical engineering of living tissues including: laboratory or medical devices that produce living artificial tissue, whether human or not, such as hearts or kidneys, etc. More specifically, the invention relates to keeping these tissues alive for sustained periods of time using a scaffold and vascular structure consistent with the tissues' authentic three-dimensional architecture, so that these tissues may be used in applications such as laboratory testing, transplantation, etc.

2. Background Art

A tissue is an aggregate of cells that form a definitive type of structural material having a specific biological function. Although a tissue can comprise a single cell type, a tissue typically comprises more than one cell type; this is referred to as a heterogeneous tissue.

The extracellular matrix is a pathway for molecular communication within and between cells, between neighboring tissues, between organs, and with migratory cells by way of: nerves, blood and lymphatic vessels, movement of small molecules in and between cells/tissues/organs, the direct contact of signaling molecules secreted by or presented on the surface of neighboring cells of the same tissues, from different organs or from the signal orchestrated movement of stem cells, or on fibers of the extracellular matrix itself, providing a mechanism for response to mechanical stimuli. Examples of tissue structures given mechanical, physiological, and functional support by an extracellular matrix include, but are not limited to: blood vessels, nerves, motor end plates, capillary beds, collecting tubules of the kidney, glomeruli, Bowman's capsule, and islets of Langerhans.

Additionally, the basement membrane system is a specialized connective tissue structure found in all tissue systems. The basement membrane system forms a continuous structure, unifying the vascular system—the circulatory interface necessary to sustain three-dimensional tissue structures. The basement membrane system is a platform essential for designing extra-cellular compartments used by the organs to house various cell types, which make up the organ's structure.

This chemical-engineering data influences how cells move, grow, and differentiate based on tissue type. These activities are responsible for changes in cell form and structure that take place when new tissues are formed and when damaged tissues are restored to good health.

The loss of or failure of a tissue or organ requires repair or replacement ofthe tissue. Tissue loss can result from, for example, injury (e.g., bums), disease (e.g., diabetes), and congenital defects. Damaged tissues/organs are often replaced with donor tissue/organs. This, however, is expensive and, moreover, there is a severe shortage of donor tissue/organs. Indeed, there is a long waiting list in this country for persons needing an organ transplant. Tissue engineering is a potential solution to address this shortage.

Tissue engineering is a technique that has the potential to create new, living tissues and organs. Tissue engineering involves providing a scaffold that can be seeded with cells for a given type of tissue that will allow the cells to develop into a tissue. The scaffold provides a mechanical support for the cells to grow on. During development of the tissue, the scaffold degrades or is metabolized, eventually leaving an engrafted tissue in its place. Current advances in scaffold fabrication techniques have allowed the formation of three-dimensional scaffolds.

A limitation in tissue engineering is that scaffolds fabricated by currently available methods lack the structural and material specificity to allow complex, heterogeneous tissue structures to be assembled. Thus, although scaffolds for developing engrafted tissues are known in the art, the tissues engineered using these scaffolds typically lack the full functional capacity of the natural tissue, due to the inability of the known methods to create the intricate vascular support system. It remains a major challenge to create three-dimensional tissue structures with precise external dimensions and internal architecture.

Initially, polymeric systems, developed with polymer scaffolds that released angiogenic factors, were used to recruit precursor cells into porous scaffolding, but these materials lacked a specific form, which would lead to thrombosis, chronic inflammation, or total rejection upon transplantation. Additionally, many of the current scaffold fabrication techniques do not allow direct incorporation of tissue-specific growth factors, without compromising bioactivity. As a result, artificially created tissues die quickly; therefore, not being able to be used in transplants or sustained for research purposes such as the development and testing of pharmaceuticals.

Since the early 1990's, with the onset of digital imaging and image processing software, such as Adobe Photoshop, the goal for manufacturers of Micro Electro Mechanical Systems (MEMS) was to create high-resolution digital photographs that were indistinguishable from traditional photography. Continued advancement in MEMS has led to the production of a charge coupling device (CCD chip) which captures images electronically at resolutions that are now exceeding the resolution of photographic films. Today's mid-level cameras can easily produce and process high-resolution images, which are very manageable on modern hardware systems. The high production capacity and the relative ease of manipulating images captured digitally has led to the production of image capturing systems in the medical industry, which traditionally use film and chemical processing to develop images. With present day image capturing systems, a big limit to the number and detail of images that can be captured, is the electronic hardware's ability to store and process data.

The need for noninvasive viewing of human organ structures in three dimensions quickly steered developers of imaging devices to produce equipment and software for the digital capture and rendering of these three-dimensional images for medical purposes. The quality of the imaging devices drove the development of instrumentation that digitally collects images of the human architecture at very high resolution, but the amount of image information captured becomes very limited due to the enormous amount of data and the lack of computer hardware capable of managing it in real time. These developments are apparent in areas such as x-ray computed tomography with the introduction of micro-computer tomography. Micro-computer tomography (micro-CT) is commonly used to generate three-dimensional tissue structures, but has found limited success because of the inability to reconstruct complete and accurate capillary beds.

Another main limitation to developing artificial tissues is the inability to mimic the microscopic architectures that is essential to the support, growth, maintenance, and function of the tissue structures. The difficulty with bioengineering blood vessels causes many researchers to focus strictly on the engineering of vascular tissues. Researchers have been unable to recreate vascular systems in three dimensions; thus forcing them to create several two dimensional sheets of tissues and layering them, in order to create a third dimension. Additionally, no one has successfully been able to manufacture blood vessels smaller than six (6) millimeters. This leads to limited functionality of the tissue and lacks the vascular organization necessary to produce variations in other organs and tissue structures.

Finally, many injuries in humans involve extensive loss of soft tissues which cannot be regenerated or repaired. Many large wounds require traumatic grafts or total amputation. The human body does not have the ability to regenerate itself due to its large body plan. If soft tissue regeneration could be enhanced, then the limb could be spared. While the large body plans of many vertebrate organisms have made it possible to mineralize tissue in order to support the soft tissue, the cellular units have remained restricted in size. As the size of the body increases, so does the area that cells have to traverse in order to cover large wounds and have become incapable of initiation of the formation of the blastemas needed for limb regeneration, as seen in smaller organisms.

What is needed is an apparatus and method to provide the intricate scaffold and vascular structure required to keep engineered tissues alive. Your applicant's method and device address the need to acquire both microscopic detail and volume, and establishes a digital archive for use in the reverse engineering of three-dimensional organ structures.

SUMMARY

In view of the foregoing disadvantages inherent in the creating of artificial tissues, your applicant has devised a device for keeping the tissues alive and a method for using the device. Hereinafter, said device will be referred to as the vascular bed chamber. The method is designed to systematically orchestrate coordinated events at different stages of a scaffold's production and subsequently the different events occurring during heterogeneous tissue development.

The method applies bio-computer aided design of cellular architecture to the use of computer aided design models as digital manufacturing code carriers that your applicant has termed: Chroma Coding or Chroma Coded code (CC-code). This CC-code is designed to carry data pertaining to the necessary environmental conditions needed to produce transformative results in tissue engineering, as well as Cartesian coordinates used for guiding robotic three-dimensional printers and three-dimensional fabricating lasers. In addition, the code will allow the user to produce models that interface directly and independently with computer guided devices to supply material such as stem cells and growth factors, and conditions such as flow rate and temperature, to the product during the manufacturing process. As a result, computer aided design models of the vascular supply systems will include complete and accurate replications of the capillary bed systems. These vascular systems will then support organ structures based on their functional morphology.

The tissues can be grown on the scaffold either in vitro (as in vascular bed chamber, configuration one, described below) to produce an engineered tissue, or in vivo (as in vascular bed chamber, configuration two, described below). Where other approaches to tissue engineering seek to design scaffolds with physical characteristics that support and maintain cell growth, your applicant has devised an approach to replicate, from material imaging data, the structural designs of the basement membrane and its interconnective extracellular support structures that are naturally found supporting the cells in the tissue structures sought to be engineered. This allows for the complete and accurate replication of the vascular structure of a tissue or organ to a degree previously thought unachievable.

The basement membrane is generally composed of two layers, one glycoprotein rich, and the other rich in collagen proteoglycans. This structure originates from the embryonic mesenchyme and surrounds all stationary cells units. Through hemidesmosomes, integrins and glycoprotein laminins, the basement membrane interfaces the cellular elements that form the smallest structural subunits in the body's tissues and organs. Along with its associated connective tissue framework, the basement membrane embraces and supports cells into units which are ultimately coupled by associated connective tissues into organs, forming multicellular organisms. It is this array of extracellular matrix surrounding organs that forms the grid of positional information, controlling pattern formation for regeneration.

The method and device also allow for regeneration of tissues and organs directly on or inside of the human body, as a regenerative process. The regenerative process for limbs or nervous tissue is promoted by creating three-dimensional stromal and cellular structures, along with appropriate embedded signaling or trophic molecules to mimic the blastema-associated limb regeneration process. Successful regeneration requires replacement of both structure and information.

The goal of regeneration is restoration of function. The limb must have regenerated muscles which are coordinately patterned relative to the joints and long bones to allow for flexion and extension, and the regenerated nerves must be patterned so as to coordinately innervate muscles. Therefore, successful regeneration requires manipulation of signaling to induce dedifferentiation to multipotent blastema cells to remake the structure, and to provide spatial information to restore function.

The novelty of this process is that it combines image data that represents both macro- and microscopic domains of tissue structures. It then uses that data for the production of the bio-informative blueprint (or Bio-CAD) which is designed to successfully interface with cells to support, recruit, and influence cellular behavior, mimicking their naturally developed tissue structures. Additionally, these bio-CAD models are converted into data files that interface with programs which drive three-dimensional fabrication and micro patterning equipment. Properly pursued, the reconstruction of tissue images into high-resolution three-dimensional CAD models that contain complete and accurate three-dimensional details of organ structures on a microscopic level is completely obtainable. With this method, the user is able to create tissue scaffolds and molecular patterned structural pathways which replicate the structural design, compelling and supporting the genesis of vascular tissue structures.

The three-dimensional digital image of bodily tissues can be obtained by a variety of methods including, but not limited to: micro-, macro-, and nano-computer tomography, nuclear magnetic resonance imaging, confocal microscopy, or reconstruction of serial sections using microscopic images. By using actual image data obtained directly from vascular tree systems, the user can create a highly detailed model of its structure.

Given the proper image data, computer aided design tools can be used to create models that accurately replicate the basement membrane system's interfacing of cellular boundaries in animal tissues. Tissue bio-fabrication begins with atomic three-dimensional images of vascular corrosion casts, representations of the geometry of the original vascular system. The images of the casts are converted into computer aided design models and combined with developmental chemical engineering data in a bio-informative blueprint, capable of guiding the computer aided manufacture of tissues, using three-dimensional robotic bio-printers and multi-photon lasers. The data in the bio-informative blueprint instructs computer aided manufacturing tools to create environments in bioreactors that mimic molecular mechanisms and cellular interactions that would normally take place in the human body when tissue is being developed or regenerated.

The bio-informative blueprint uses micro-prototyping techniques such as: the three-dimensional chemical patterning of photo-cross linkable multilayered hydrogels, the complete structural fabrication of vascular scaffolding—scaffolding that will support, nurture and guide the cellularization of microvascular and macrovascular structures, and serve as a nurturing framework. The scaffold can be divided into a plurality of regions, and each region can have a different structure. The term structure, in this context, refers to the characteristics of the region that enable a specific tissue type to develop at that region. The structure at a region not only includes the components that provide a structural support for the tissue to grow at that region, but can also include other components that facilitate cell growth such as, but not limited to: growth factors, nutrients, and patterned development of vascular and lymphatic support systems and nerve fibers, with their corresponding connections to the central nervous, cardiovascular, and lymphatic systems. Additionally, this framework supports the further engineering and design of organ specific, functional tissue structures from chemically and mechanically engineered extracellular matrices, using micro-rapid prototyping and three-dimensional laser pulse patterning for the regulation of tissue specific cellular morphologies.

The resulting scaffold provides a support that allows the growth of a tissue. The scaffold provides an environment that guides growth of each individual tissue type, so that each tissue type is geometrically arranged to recreate the tissue's unique cellular design and to reestablish the complex biological interrelationships that are responsible for a given tissue's function. The method permits different regions of the scaffold to be strategically composed of specific material(s) that have structure and components that are conducive to the growth of a particular type of cell. The scaffold obtained by your applicant's method can, for example, include regions that are conducive to growing blood vessels. Scaffolds obtained by typical fabrication processes cannot provide for the growth of blood vessels.

BRIEF DESCRIPTION OF THE DRAWINGS

The invention will be best understood by those having ordinary skill in the art by reference to the following detailed description when considered in conjunction with the accompanying drawings in which:

FIG. 4 illustrates a close-up, perspective view of the support bar that aids in the expansion of the first embodiment for supporting the creation of tissues or organs outside of the body.

FIG. 5 illustrates a perspective view of the first embodiment within a support chamber to show the interrelationship between the first embodiment in an upside down collapsed state and the support bar that expands the first embodiment for supporting the creation of tissues or organs outside of the body.

FIG. 6 illustrates a sectional view of the first embodiment with a completed artificial heart.

FIG. 8 illustrates a perspective view of the blastema-inducing film created to overlay the wound and stimulate tissue or organ growth directly on a human body.

FIG. 9 illustrates a mold of the wound to be repaired containing a heating element to mold the film from FIG. 8 to be a direct overlay match of the actual wound for tissue or organ repair directly on the human body.

FIG. 14 illustrates the input port with tubules extending from the bottom of the port directly on an open wound that will allow for the inflow of cells and other substrates for tissue and organ repair directly on the human body FIG. 15 illustrates the inlet port that is expandable, collapsing over the tubules which are foldable, to allow extraction from the wound for tissue or organ repair directly on the human body.

DRAWINGS—REFERENCE NUMERALS

Figure 1:
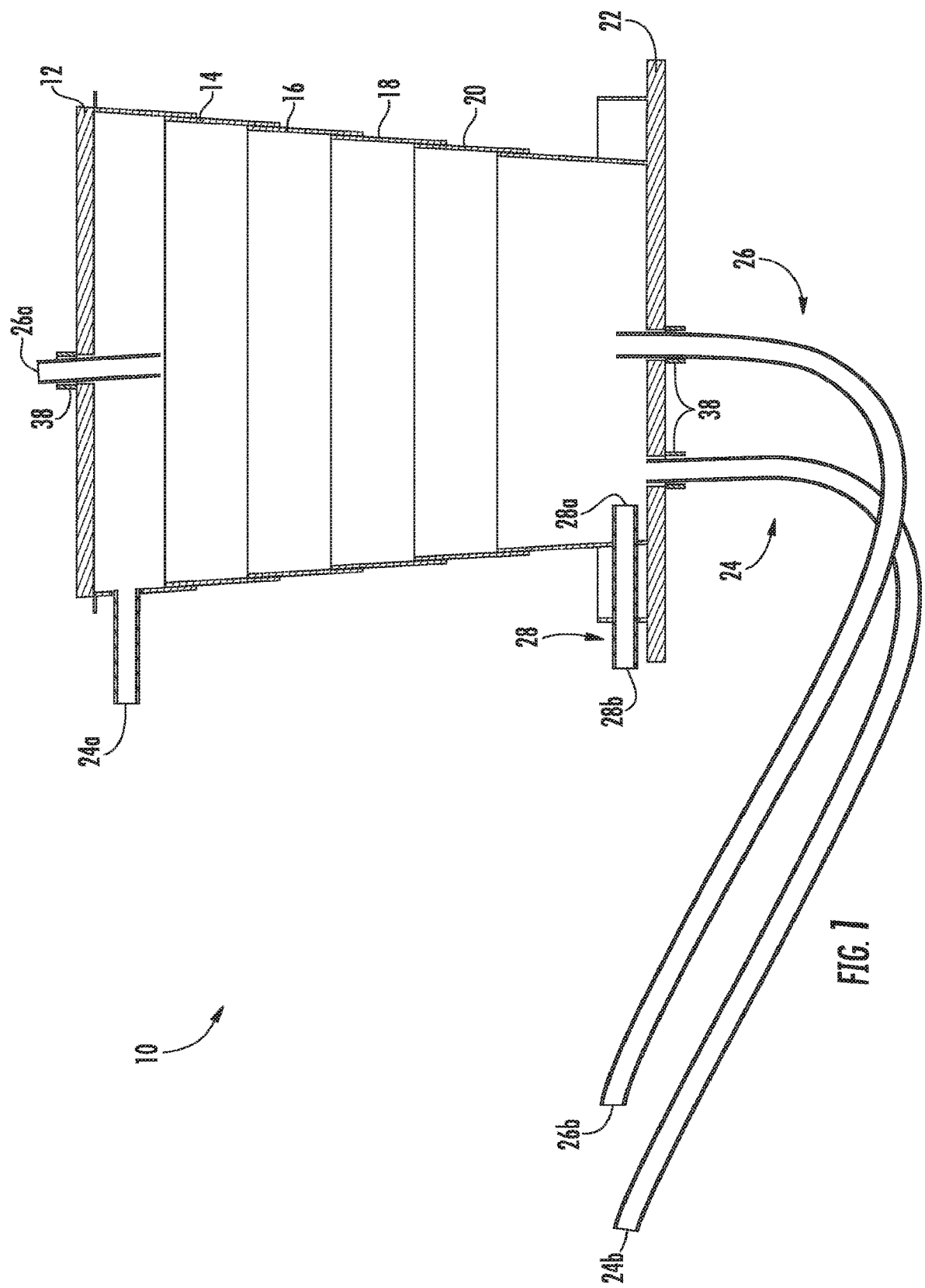
FIG. 1 illustrates a sectional view of the first embodiment of the apparatus in an expanded position for supporting the creation of tissues or organs outside of the body.

10 Vascular Bed Chamber first configuration (VBC-I)
12 Top of VBC-I
14-20 Tapered expandable/collapsible sides
22 Base
24 Input/output tube
  24a Input port
  24b Output port
26 Input/output tube
  26a Output port
  26b Fabrication site
28 Input tube
  28a Outflow into chamber
  28b Input port
38 Locking spacers
100 Production/Inversion chamber for housing VBC-I
102 Support rod
104 Sleeve to support slider (112)
106 Adjustable slider
108 Upper clamps attached to the support rod (102) to hold the bottom of the inverted VBC-I during production
110 Spring loaded lower clamps to hold the top of the inverted VBC-I during production
112 Slide that allows support rod to move in a vertical plane
114 Inflow port to attach to inflow port 24 directly on VBC-I
116 Outflow port to attach to outflow port 28 directly on VBC-I
120 Adjustable knob attached to support rod to allow for the vertical movement of support rod
122 Thermal regulated stage at the base of inversion chamber to support VBC-I
124 Outflow port to attach to outflow port (24) directly on VBC-I
126 Outflow port to attach to outflow port (26) directly on VBC-I
128 Additional, optional port if needed
130 Transparent portion in middle of base
132 Seal between the thermal regulated base (122) and the transparent middle section (130)
200 Vascular Bed Chamber second configuration (VBC-2)
202 Patient wound
204 Blastema Induction Film
206 Individual sections that fit together to form the entirety of VBC-2
208 Inner support tube for flow of cells and substrates into small tubules for production
210 Fabrication laser
212 Inward flow tube for cells and other substrates
214 Lip allowing (212) to slide over (208)
216 Threads for attaching additional sections or digit sections (244)
218 Outflow ports for recirculation
220 Protective hydrophilic gauze 222 Fatty acid mixture with intergins
224 Wax paper
226 Division creating hydrophobic and hydrophilic regions of intergins
228 Hydrophilic region
230 Hydrophobic region
232 Wound mold
234 Heating element
236 Circulation channels
238 Female opening for section attachment
240 Male protrusion for section attachment, locks in to (238)
242 Inflow ports
244 Chamber for regeneration of digits for attachment to VBC-2 sections (206) via ports (216)
246 Retractable tubules for the placement of cells and other substrates directly on an open wound
248 Outflow ports on tubules (246)
250 Female threads on laser fabrication goggle
252 Transparent base on laser fabrication goggle
254 Laser fabrication goggle with immersion oil for encasing microscope objective lens

DETAILED DESCRIPTION

Many different systems having features of the present invention are possible. The following description describes the preferred embodiment of select features of those systems and various combinations thereof. These features may be deployed in various combinations to arrive at various desired working configurations of systems.

Reference is hereafter made to the drawings where like reference numerals refer to like parts throughout the various views.

Method

The best description of the method is blastema based regeneration, but the procedure is not that simple. It could also be considered computer aided tissue engineering/biofabrication, but not in the traditional sense. This method enables the digital manufacturing of composite structures, optimizing automated use of the simplest design up to the largest data sets, allowing for production schemes on any scale imaginable. The following things will be needed to produce blastemal based regeneration of tissues: three-dimensional reconstructions of sectioned tissues and castings of the tissues, computer aided design of cellular architecture, three-dimensional regenerative blueprint, robotic production of a bio-stimulatory scaffold, vascular bed chamber (either free standing—VBC-I, or form fitted to the patient's specific needs—VBC-2).

Tissue bio-fabrication begins with atomic three-dimensional images of vascular corrosion casts, representations of the geometry of the original vascular system. The images of the casts are then converted into computer-aided design models and combined with developmental chemical engineering data in a bio-informative blueprint, capable of guiding the computer-aided manufacture of tissues using three-dimensional robotic printers and multi-photon lasers. With this process, the production of these composite structures can be bio-manufactured digitally, producing cellular-based advanced materials that can regulate the regeneration of three-dimensional tissue structures or organs.

The preferred method for obtaining the three-dimensional image is decellularization of tissues, leaving the extracellular matrix. Then having a clear picture of the matrix by staining the matrix with heavy metals, such as osmium, and capturing the images of the extracellular matrix at three levels of resolution, using conventional computer tomography, micro- and nano-CT, and reconstructing the tissue's extracellular matrix from serial scans using a progressive removal of layers of the extracellular matrix.

Given the proper image data, computer aided design (CAD) tools can be used to create models that accurately replicate the basement membrane system's interfacing cellular boundaries which create the natural, modular compartmentalization found in animal tissues. Where other approaches to tissue engineering seek to design scaffolds with physical characteristics that support and maintain cell growth, your applicant's method is to replicate, from medical imaging data, the structural designs of the basement membrane and its inter connective cellular support structures (also known as the septa) that are naturally found supporting the cells in the tissue structures sought to be engineered.

These modeling results can be the basis for designing a bio-blueprint. The bio-blueprint uses micro-prototyping techniques, including but not limited to: the three-dimensional chemical patterning of photo-cross linkable multilayered hydrogels. This allows the bio-blueprint to guide the more complete structural fabrication of a vascular scaffolding—scaffolding that will support, nurture and guide the cellularization of microvascular and macrovascular structures and serve as a nurturing framework. This framework supports the further engineering and design of organ—specific, functional tissue structures from chemically and mechanically engineered extracellular matrices, using micro-rapid prototyping and three-dimensional laser pulse patterning for the regulation of tissue specific cellular morphologies. These steps create a virtual design of the tissue, or a bio-CAD, and once the bio-CAD has been completed it can be archived in a virtual library and establish a virtual tissue bank.

Using CAD, these archived models can then be manipulated, with minimal effort, to meet a patient's specific needs. A very high level of precision, capable of working at microscopic dimensions, facilitates the manufacture of tissue structures and/or extracellular matrices that will support bio-fabrication. This procedure leads to the production of authentic tissue structures for use in partial or total organ or tissue replacement or transplant therapy.

The method can be broken down into the following steps, which will be elaborated on, individually, below.
1. Select organ/tissue structures.
2. Isolate the organ or tissue's vascular structures using vascular casting.
3. Isolate the organ or tissue's septa systems, including the organ or tissue's authentic encapsulating boundary structure (for example: pericardium, endocardium, periosteum, endosteum, perineum, endoneurium, etc), by de-cellularization and or the selective staining of its septa systems
4. Capture image of the septa, compartmenting connective tissue boundaries, and vascular systems
5. Use images above to create three-dimensional models of the structure
6. Import the three-dimensional models into computer-aided design software
7. Repair the models using CAD tools and convert mesh into non-uniform rational B-spline models
8. Designate the boundary where the septa and vascular cast interfaced cells as site of the basement membrane
9. Use computer-aid design (CAD) tools to clean up the basement membrane system's boundaries and model the walls of the vascular tree system for the scripted production schema
10. The tissue's structures are broken down into their structural sub-layers/subunits. For each sub-layer/subunit categorize:
    the cell types that form the layers/subunits,
    the structural and functional material constituting in the extracellular matrix within each type of layer/subunit,
    growth factors needed to induce cells to produce the different cell and extracellular matrix types that form tissue structures within the layers/subunits
    cytokines/chemotactic factors that need to be released to attract native adult stem cells from the body's tissues into specific sites of the fabricated scaffold
    extracellular signaling factors such as structural molecules with ligands that signal the cells to form tissue structures within the layers/subunits
    the functional peptides that constitute the above ligands responsible for the extracellular signaling factors
    determine which ones need to be attached to the scaffold
    patterning their attachment location within the scaffold
    Cells used in the natural developmental/regenerative processes
    Cells to be used in fabrication processes
    Encapsulating extracellular signaling factors within molecular cages/nanospheres
    Laser and biochemical techniques for attaching molecular cages/nanospheres to the scaffold during and after the bio-printing processes
    Laser, bio-degenerative and enzymatic techniques for a patterned time release of functional peptides, growth factors and chemotactic factors from molecular cages/nanospheres at scripted time intervals
    Biochemical and laser techniques for attaching functional peptides to scaffold
11. Chart the epigenetic information on the organ's/tissue structure's natural development/regeneration to correspond with the available CAM tools, their specifications, construction materials and supported bioreactor processes
12. Use the chart from step 11 to script into Bio-CAD code for a production plan producing and transmitting signals that control the computer-aided manufacturing/tissue engineering tools' robotic placement of construction materials; robotic positions and triggering of laser tools for molecular/atomic manipulation of said materials; bio-support of living fabricated structures using vascular and interstitial fluid circulation;
13. Time the stimulation of tissue growth by regulating environmental factors, forces applied to, temperature, concentration chemicals of developing structure using fluid circulation and laser motivated chemical reactions to coordinate with feedback sensors for temperature, pressure and chemical concentration of oxygen and carbon dioxide.
14. Map the expression of growth/differentiation factors
15. Use the Bio-CAD blueprint to coordinate the delivery/triggered release of conditioned growth media, cells, chemotactic and developmental growth factors with the robotically controlled manufacturing process to mimic and induce the cellular environments that naturally occur in the developmental/regenerative tissue structure.
16. Modify Bio-CAD design for using CAD tools to create paths and locations for each fabrication step. Duplicate CAD structure for each independent fabrication step
    a. Replicate the vascular tree model; make it a solid form
    b. Offset model's location in the septa to model the paralleling nerve fibers found in the tissue's septa.
    c. Again replicate the vascular tree model and offset its location in the septa to model the paralleling lymphatic vessels, alternatively lymphatic systems can be cast and modeled uniquely.
        i. Tubular systems i.e. kidney collecting tubules, loops of Henley, where present, are cast and modeled separately.
        ii. Size and position the locations of each of these models to locations in the modeled septa to correspond with their natural size and location.
17. Use Bio-CAD and apply Cartesian coordinates to each sub model as creating unique groups of coordinates for conveying scripted roles to CAM instrumentation in the production schema.
18. Associate the production schema with the appropriate Cartesian coordinates to programs that guide CATE Strategies and CAM Tools by:
    a. Coding the production scheme for each uniquely modeled tissue structure by creating a table with 18 single digit values of 0-9.
    b. Assign the code to the materials and the processes used in the production scheme for fabricating each structure in the CAD model.
    c. Divide table into six categories each represented by three digits.
    d. Assign categories to each of the following color components: Hue; Saturation; Value; Red; Green; Blue.
    e. Use a common graphic software color picking tool to covert the above code into color.
    f. Apply the computed color above to the boundary representation for each set of Cartesian coordinates established to represent a tissue's structures.
19. CAM tools take instructions from the colors used in CAD blueprints by decoding the color values at specific Cartesian coordinates assigned to a tool.

The first step requires identifying the composite tissue and collecting the image data on the structure. Organs will be injected with material that shows up on x-ray, either within the intact organ so that subsequent histological analysis can be performed and related anatomically to the vessels, or with a casting material that can be isolated from the tissue by selective dissolution of the tissue with a caustic solution. This casting method allows for higher spatial resolution. For organs where different vascular or tubular structures have to be differentiated (for example: bronchioles from blood vessels, bile duct from hepatic vessels, or the portal vein from the hepatic artery, etc), contrast/casting materials doped with nano-particles consisting of different metals should be used so that the different K absorption edges can be identified. Additionally, the sample should be scanned in the X and Y planes, and different layers will be fabricated by scanning the sample in the Z direction; thus, allowing nanostructures to be fabricated. Three-dimensional laser patterning enables models, created following this process, to create a structural framework that both physically and biochemically guides the genesis of the original organ structure by incorporating factors responsible for stimulating optimal cellular and sub-cellular responses that mediate cell behavior for bioengineering the tissue structure.

Once the tissue or organ to be replaced has been identified, a vascular scaffolding will be designed directly from three-dimensional image data. This complete vascular network will also include the capillary systems necessary to feed the surrounding tissues. Sections are then converted to three-dimensional wire frame models and are then merged together using computer aided design (CAD) software. Reconstructed image data sets from Micro-CT and serial sectioning of the corresponding capillary beds are combined to complete the framework for the CAD model (also referred to as a bio-CAD model, or a bio-informative blueprint, or bio-blueprint). This produces a framework in a complete three-dimensional layout of the inner wall of the vascular tree system in the tissue or organ of interest. CAD can then be used to render, on top of the layout for the lumen wall, a design for structural scaffolding structured for seeding migrating progenitor and/or stem cells. The data in the bio-CAD will instruct computer aided manufacturing tools to create environments in bioreactors, that mimic molecular mechanisms and cellular interactions that would normally take place in the human body when tissue is being developed or regenerated. Then CAM uses three-dimensional robotic bio-printers and multi-photon lasers to produce an authentic three-dimensional tissue structure.

A bio-CAD blueprint is formed using a system comprising at least one computer that uses data collected on the authentic microscopic architecture of tissue structures from tissue specimen preparation techniques that include but are not limited to:
  Lumenal corrosion casting used to create luminal boundaries such as: vascular lumen, endocardium, gastric lumen, intestinal lumen, etc; and
  Decellularization and molecular labeling of marginal boundaries in cell structures such as: connective tissue capsule, connective tissue septa, myocardium, pericardium, endocardium, etc.

Data gathered from tissue specimen preparation represent the spatial arrangement of cells living within the boundaries of their mechanical, physiological and functional supportive extracellular matrix—the structural formation of a given tissue. The architectural arrangement of an organ's extracellular matrix serves, not only as boundaries between cells and their tissue forming units, but is also a source of support at varying levels of defined cellular organization.

Next, using Chroma Coded Manufacturing (CCM), chroma codes are created to guide the production of the composite structures through the use of computer aided design software to model the structure. CCM consists of points, lines, and/or surfaces used in CAD to create three-dimensional models of composite structures that are assigned colors, representative of chromatically converted chroma codes embedded in the bio-CAD blueprint to direct the necessary materials and conditions needed for the manufacturing process. Chroma coding directs the accumulation and positioning of factors needed for the manufacturing of and the stimulation of cellular constructs and their sub-cellular responses. Chroma coding enables models to provide detailed information guiding the manufacturing nests and paths for cells, during fabrication, creating a structural framework that both physically and biochemically guides the genesis of the original organ structure. A three-dimensional tissue blueprint needs to be prepared from data on tissue development to orchestrate the release and selective attachment of functional peptides to polymerize hydrogel events initiated by the computer integrated micro-fabrication tools.

Chroma codes are created for compartments represented by a combination of the numbers "0-9". Within these compartments are sorted production data, such as the advanced materials being used in the manufacturing process; their three-dimensional placement by robotic positioning of materials during production; the environmental conditions needed during production for bio-manufacturing process; and the time intervals between processes within a manufacturing scheme. The resulting chroma codes are chromatically converted into colors, corresponding to the codes' series of ordered numbers. These numbers are embedded in the colors of the bio-CAD model and are retrieved from the design by a tri-stimulus colorimeter and placed in the compartments assigned, in order to regulate the productions schemes in the robotically controlled devices.

The following is a list of steps to create a chroma code:

- Chart the epigenetic information on the organ/tissue structure's natural development/regeneration to correspond with the available CAM tools, their specifications, construction materials, and, where needed, the supported bioreactor processes.
- Script this chart into the bio-CAD code for a production plan producing and transmitting signals that control the computer aided manufacturing tools' robotic placement of construction materials, robotic positions and triggering of laser tools for molecular/atomic manipulation of materials, bio-support of living fabricated structures using vascular and interstitial fluid circulation.
- Time the stimulation of tissue growth by regulating environmental factors, forces applied to: temperature, concentration of chemicals of developing structure using fluid circulation, and laser motivated chemical reactions to coordinate with a feedback sensor for temperature, pressure, and chemical concentration of oxygen and carbon dioxide.
- Map the expression locations and/or release locations of tissue growth and/or differentiation factors and other chemical engineering data needed to guide tissue production, within the appropriate CAD structures.

Once the chroma codes have been completed and integrated into the bio-CAD, the bioCAD will first code a vascular scaffold. This vascular scaffolding will be designed and made using three-dimensional fabrication techniques, including the use of photon laser techniques used in the micro-patterning of the molecular structures of materials. Computer-aided modeling of stereolithographic (STL) and micro-computer tomographic (micro-CT) models enables the user to design the vascular tree system, including capillary beds. Reconstruction in stereolithography format allows compatibility of micro-CT derived three-dimensional models with most CAD software. Noise from the datasets will also be removed using interactive parallel visualization and graphical analysis for contour plotting and generation of STL files. By being able to reduce the noise, the memory footprint is also reduced, making the file smaller and more manageable. Additionally, corrosion casting of luminal structures also provides accurate and high-resolution results for three-dimensional micro-CT reconstruction of capillary beds. Using a nanotip and nanopore array will influence cell differentiation, proliferation and growth. Using cylindrical circles of the nanotip and nanopore arrays will stimulate vascular tissue growth.

In other words, it begins by creating a bio-blueprint, also referred to as a bio-CAD, and identifying the tissue or organ to be transplanted or regenerated. The blueprint can then be designed, through reverse engineering, of the organ's connective tissue structure and extracellular matrix. This bio-informative data is used to produce developmental patterns which produce signals transmitted to the computer aided manufacturing or tissue engineering tools. The design will represent the extracellular matrix environment and stimulate the necessary cell-type specific behaviors. Data instructs computer aided manufacturing tools, including bioreactors, spatially and temporally, to perform tasks during the fabrication process that allows the fabricated structure to experience environments designed to mimic molecular mechanisms and cellular interactions found in the natural development or regeneration of biological tissues.

Creating a functional three-dimensional tissue structure provides a platform for the design and engineering to support the growth and differentiation of cells into their specific phenotypes to make up a tissue or organ. The extracellular matrix is incorporated into this platform. The most important of the extracellular components that make up the matrix, the basement membrane (or basal lamina), is the core support structure, and thus, the most critical component in the platform. This design stimulates the necessary cell-type specific behaviors. Tissue scaffolds can be designed using microscopic image data that guide the generation of blastema-like cell masses and their subsequent regenerative processes. These scaffolds then guide and support the regeneration of the composite tissue structure.

The next step involves designing the three-dimensional models of the image data, and incorporating molecular and environmental factors that mediate cellular and subcellular behaviors, responsible for generating the tissue and/or organ structure. The process begins by coding a script containing bio-informative data and layering this information into a bio-blueprint of the patterned response designed to mimic the chemical engineering data gathered from a tissue's developmental process. The blueprint sends scripted signals, via computer, to manufacturing tools in progressive steps that are designed to create the regenerative processes through the tools' responses. These responses are designed to respond to environmental feedbacks measured from fabricated structures. These activities are responsible for producing the changes in cellular development and regenerative processes. The fabricated structure will also assist the molecular mechanisms which are the basis of communication between cells themselves, and between cells and their extracellular matrices, and are responsible for forming the germinal cell layers in humans: endoderm, ectoderm, and mesoderm and the subsequent tissue types (for example: epithelium, skeletal muscle, cancellous bone) and their subsequent organ systems (for example: cardiovascular, endocrine, or nervous systems). These interactions include molecules that interact, causing changes in molecular confirmations which initiate G protein-coupled receptor mediated events that culminate in the initiation of biochemical mechanisms on and within cell membranes, cytoplasm and the nucleus. By this means, the blueprint will initiate and regulate the necessary cell processes with the cell organelles that procure them into the tissue regenerative process.

Image data can also be obtained from reconstructing serial sections acquired from histological techniques, taken through a reference plane created during tomography scans.

Reference points are created in scanned tissue that corresponds with section tissues. The resulting images are imported into bio-CAD software where the afferent and efferent arterioles and venules mesh structures obtained with Micro-CT are connected with mesh structures obtained through the reconstruction of serial tissue sections from the capillary bed systems. Image data/information from tissue structures is used to create computer-assisted designs of these structures modeled to create a structural framework, both physically and biochemically for regenerating the original tissue structure around the vascular tree systems. Molecules (e.g. growth factors or cytokines) responsible for stimulating optimal cellular and sub-cellular responses are incorporated into these vascular scaffolding designs.

The three-dimensional digital image is superimposed on a three-dimensional grid, having a plurality of axes in the X, Y, and Z directions. There is no preferable distance between each axis. The distance should be determined based on the specification of the needed tissue or organ structure, and typically set to fall within the resolution of the robotics or materials needed in a particular fabrication scheme to produce a necessary structure in the scaffold design. Robotic printing is typically between five and two hundred microns, while laser fabrication or molecular manipulation can use distances in a nanometer scale. There are variables to consider in determining the distance between each axis including: the size of the material being robotically deposited, the spot size of the lasers being used for photo initiated chemical activities such as photopolymerization of hydro gels into a network of tracts that guide and support cells in developmental precessions. Examples include, but are not limited to: blastema cells, mesenchymal cells, pericytes/fibroblast cells which migrate along the surface of scaffolds depositing fibronectin, collagen, and other molecules in the extracellular matrix. These distances are used to support the fabrication of the extracellular tracts and fine structures needed to support cellular behavior. The smaller the distance between axes, the more extracellular detail can be given in the scaffold, providing for an engrafted tissue with much finer detail.

Each place that is sectioned by the grid and having an intersecting point with the X, Y, and Z axes is given a designated point in three-dimensional space, so as to provide a plurality of points. Each point can then be identified as corresponding to a tissue type. Guided blastemal formation is achieved by using coordinated spatial and temporal molecular communication to dedifferentiate cells on surface interfacing zones needing composite tissue regeneration. Guided blastemal formation can also be attained by recruiting dedifferentiated cells along three-dimensional paths and gradients that were prepared and initiated by laser guided molecular manipulation and orchestrated by tissue engineering blueprints.

The bio-fabrication process involves signaling that is elicited electronically, chemically, and mechanically, and occurs between cellular systems and technology. Computer aided manufacturing (CAM) uses three-dimensional robotic bio-printers and multi-photon nanolasers. Bio-printers are used to strategically place cells and construction materials from the bio-CAD blueprint's assigned locations. Multi-photon lasers are used to initiate chemical processes such as: the polymerization of a hydrogel scaffold, the attachment of a chemical cage/nanosphere, and/or the release of the contents encapsulated in said spheres producing the desired developmental results.

The next steps include using the three-dimensional model to interface computer programs for fabrication, and then using those three-dimensional models to direct micro-patterning and release of molecular factors that regulate cell migration, cell proliferation, cell differentiation, and cell chemical production in three-dimensional fabrications. Data/information is taken from tissue structures to create computer assisted designs of these structures. The computer aided manufacturing is used to fabricate a scaffold that is sectioned from the grid discussed above. The program fabricates the scaffold by reproducing each point from the three-dimensional image that is sectioned by the grid as a corresponding point on the scaffold. Then a microcomputer tomography image of vascular tissue is combined with the reconstruction of thin serial tissue sections. The resulting bio-CAD rendering produces a structural design for scaffolding on which a vascular tree can be constructed.

Essentially, the scaffold is created by replicating the vascular tree model in a solid form. Then the model is offset from its location within the septa to allow a model of the paralleling nerve fibers found in the tissue's septa. Next, the vascular tree model is replicated again and offset in the septa to model the paralleling lymphatic vessels. An alternative to this step would be that the lymphatic system can be cast and modeled uniquely. For example, tubular systems, such as kidney collecting tubules, can be cast and modeled separately. The size and position of the locations of each of the models to the locations modeled in the septa correspond to their natural size and location.

Next, use the three-dimensional model to direct three-dimensional fabrication techniques to create structures that support and regulate tissue/organ genesis using the following procedure. Create structural environments that regulate cell behavior, cell functions and pattern their locations to correspond with image data/information taken from tissue structures during the data collection and CAD modeling stages of this method. Create a structural framework using any three-dimensional fabrication techniques. This includes but is not limited to the use of photon laser techniques used in the micro patterning of the molecular structures of materials, such as hydrogels, and incorporating into these structures factors that are responsible for stimulating optimal cellular and sub-cellular responses that mediate cell behaviors.

Alterations should be made using computer directed two or three photon lasers, which alter the molecular structure of polymers in areas that produce the cellular responses such as migration or lack of cell penetration, that outline the structural design formed in bio-CAD based on the original image, molecular and environmental factors data acquired during the collection stages above. Use the three-dimensional model to pattern specific molecular factors to form the capillary beds, which are vital to molecular exchange in and between cells living in and around vascular tree structures.

The three-dimensional model is then used to pattern the formation of vascular trees, the capillary beds, extracellular matrix and cells living in and around them to form the basis for the three-dimensional tissue growth necessary for organ development. Pattern cell migration, cell proliferation, cell differentiation and cell chemical production in three-dimensional fabrications to correspond to the original image, including molecular and environmental factors, data acquired to create structural environments that regulate cell behavior and cell functions. Use the image data/information taken from tissue structures to create computer assisted designs of these structures modeled to create a structural framework, both physically and biochemically for tissue genesis of the original structure.

In building the various scaffolds, bio-blueprints are used to guide the creation of structural and chemical environments that regulate cellular behaviors and/or functions. Many combinations of steps will result in the formation and/or production of composite tissues based on three-dimensions. Some examples of the interrelationships between steps and this method include but are not limited to the following relationships:

- Directing computer programs that alter the molecular structure of polymers in areas that produce the cellular responses based on the three-dimensional model;
- Directing the housing and releasing of factors that are responsible for the cell's morphogenesis, based on a three-dimensional model;
- Directing computer programs to direct factors to control cell production and/or the release of growth factors, cytokines, and chemokines based on a three-dimensional model;
- Directing the regulation of migration, proliferation, differentiation, and chemical production of cells based on a three-dimensional model;
- Directing organ genesis in a vascular bed chamber, based on a three-dimensional model;
- Directing fabrication of the chosen organ tissues in body cavities, in wounds, and surgically created spaces based on a three-dimensional model.

The next step uses the three-dimensional models to direct composite tissue regeneration. The vascular bed chamber regulates vascular flow and media content using sensors that generate and feed data back to a computer capable of regulating the dispensing of molecular and environmental factors that control cell behaviors such as migration, proliferation, differentiation and chemical production in a bioreactive environment.

CAD models of casts representing a vascular tree's lumen are used to provide the framework for data concerning sizes and dimensions that will direct fabrication of scaffolds in a vascular bed chamber capable of establishing tissues that mimic the original vascular tree. In the vascular bed chamber, a volume flow pumped to simulate a vascular circulatory system creates variable forces on the tissue structure. Combined with external structural supportive forces, the vascular bed chamber regulates the structural properties of developing blood vessels and surrounding tissues.

Following this, the three-dimensional model is used to direct fabrication of the chosen tissue/organ in body cavities, wounds, surgically created spaces, or directly in a vascular bed chamber. First, alter the structure of reactive polymers such as photosensitive polymers, which are placed into a body cavity, and/or wound, and/or a surgically created space, and/or vascular bed chamber—in patterns consistent with the three-dimensional models.

Then, use injectable polymers as a foundation for structural environments that regulate cell behavior, cell functions, and pattern their locations to correspond with image data/information taken from tissue structures during the data collection and CAD modeling stages of this method. Polymers are altered in three-dimensional patterns, directed by the bio-CAD model to create a structural framework using any three-dimensional fabrication technique. This includes but is not limited to the use of photon laser techniques used in the micro patterning of the molecular structures of materials, such as hydrogels, and incorporates into these structures factors that are responsible for stimulating optimal cellular and sub-cellular responses that mediate cell behaviors.

Make alterations using computer directed two or three photon lasers, which alter the molecular structure of polymers in areas that produce the cellular responses, such as migration or lack of cell penetration, which outline factors of molecular and environmental data acquired during the collection stages above, and regulates in patterns consistent with three-dimensional models initiating the formation of natural vascular tree structure and other tissue structures, such as alveolar sacks or nerve tracts, in body cavities, in wounds or in surgically created spaces.

Use the three-dimensional model to pattern specific molecular factors to form the capillary beds, which are vital to molecular exchange in and between cells, living in and around vascular tree structures in body cavities, in wounds, in surgically created spaces or in one of the vascular bed chamber configurations. Then, use the three-dimensional model to pattern the formation of vascular trees, the capillary beds, extracellular matrix and cells living in and around them to form the basis for the three-dimensional tissue growth necessary for organ development in body cavities, in wounds, in surgically created spaces, or in a vascular bed chamber. Pattern cell migration, cell proliferation, cell differentiation and cell chemical production to correspond to the original image, including molecular and environmental factors data acquired to create structural environments that regulate cell behavior and cell functions in body cavities, in wounds, in surgically created spaces or in a vascular bed chamber. Use three-dimensional model to direct the fabrication of physical and biochemical structural frameworks that stimulate regeneration of organ structure in body cavities, in wounds, in surgically created spaces, or in a vascular bed chamber.

Next, use the three-dimensional modeling computer program to direct the alteration of the molecular structure of polymers in areas that produce cellular responses. Alter the structure of polymers in three-dimensional patterns, directed by the bio-CAD model, using image data/information taken from computer assisted designs of the needed tissue structures. Design a model to replicate the structural framework, both physically and biochemically, for tissue genesis of the original structure. Then, build around vascular tree systems formed in accordance with the previously described process of vascular scaffold designing. Fabricate, directly from three-dimensional image data, an in vivo occurring vascular network that includes the capillary systems, which are necessary to feed the surrounding tissues. Incorporate into these designs using any three-dimensional laser, two or three photon laser techniques, factors which are responsible for stimulating optimal cellular and sub-cellular responses that mediate both normal and abnormal cell behaviors that outline the natural vascular tree structure or other tissue structures such as alveolar sacks or nerve tracts.

Next, using the three-dimensional model, house and release previously described molecular factors for cell morphogenesis in fabricated photo reactive material. Using the three-dimensional model, trigger the release using laser patterning of factors responsible for cellular morphogenesis based on spatial and temporal patterns of growth factor signaling in order to form tissue structures such as the tunic layers found in blood vessel walls.

The chroma coded bio-CAD will plot the position, the photo polymerization, and photo activated release of molecularly caged developmental factors, by robotically positioning the photon emitters using multi-photon femtosecond lasers and robotic dispensing tools. It is best to use a femto tunable laser based STED system in combination with a scanning confocal microscope. STED technology is used to overcome any diffraction limitations for multifunctional instruments.

STED is an implementation of a family of scanning far-field optical techniques and extends a confocal laser scanning microscope by providing an additional illumination path for fluorescence depletion. STED uses two laser beams having different wavelengths (or colors), instead of a single source of light in conventional photolithography. Typically, two lasers are used, violet—the normal excitation laser, and green—having a donut configuration. The green laser depletes all of the fluorescence generated by the excitation light and only the tiny middle hole will radiate fluorescence. This unique system can overcome conventional diffraction limits to achieve nanoscale spatial resolution for the fabrication of nanostructures.

When the activation beam has a higher laser power and activates the resist to cause cross-link to make patterns on the resist layer, the inhibition beam suppresses the activation while maintaining a valley at the center of the activating beam. The outcome of the activation peak and "deactivation" donut pattern gives a spatial dosing pattern that is substantially smaller than the far-field diffraction pattern of a tightly focused optical beam. The deactivation of the resist is reversible, i.e. when the deactivation light is removed, the resist can again photo-polymerize when it is exposed to the excitation light. Thus, nanostructure can be patterned by scanning the laser beams on the resist. The activation and deactivation can be achieved by optimizing the laser intensity and timing of the laser pulse. The deactivation beam controls the spatial distribution of exposure, and thus the resolution. Furthermore, the donut inner diameter can be decreased by increasing the intensity of the donut beam. In this way the resolution of patterning can be significantly increased to overcome diffraction limit and pattern nanostructures.

The method discussed above can be used to generate tissues both externally, for transplantation, or directly on/in the human body, for regeneration. This section will focus on the intricacies associated with the method in relationship to the regenerative process and using the second configuration of the vascular bed chamber.

The bio-CAD is formed by converting three-dimensional CT scans of the wound or defect, in order to produce custom scaffolds to fit the specific defects. The blueprint is designed to produce a three-dimensional substrate which will guide the cells in the body to form a regenerative blastema for the organ or tissue to be regenerated. The subsequent blastema is guided and sustained in a form fitted regenerative chamber, the second embodiment of the vascular bed chamber (VBC-II) described below, where it generates the necessary composite of tissues needed to replace missing, damaged, or diseased organs or tissues.

The regenerative process is promoted by creating three-dimensional stromal and cellular structures along with the appropriate embedded signaling or trophic molecules to mimic the blastema-associated regeneration process. The initial signals for regeneration are growth factors. The initial target of nerve signaling is the apical wound epithelium This epithelium is functionally equivalent to the apical epithelial cap in developing limbs, and is required for both outgrowth and pattern formation. Apical epithelial cap function is dependent on basal keratinocytes withdrawing from the cell cycle, and that cell cycle withdraw is induced by nerve signaling and is maintained by gap junctions between adjacent basal keratinocytes. Expression of the marker for apical epithelial cap dedifferentiation can be induced by keratinocyte growth factor (or FGF7), which is produced by injured or regenerating nerves. The downstream targets of nerve or apical epithelial cap signaling are the mesenchymal cells of the blastema. The generation of a blastema at the site of injury is a critical step for limb replacement. A blastemal-inducing film (discussed below) is created and placed over the wound. The bio-CAD blueprint will aid to signal and regulate the growth factors in the proper time and space, promoting regeneration directly on or in a human body.

A synthetic blastema is stimulated to form along the margins of the VBC-II (the construction of which is discussed below) and ties into the main vascular supply for the region to be regenerated. The VBC-II is placed on the wound or in the body and attached to bypassed blood vessels and acted upon by the bio-CAD blueprint. This enactment establishes the complex biological interrelationships between cells responsible for the formation of tissues.

The VBC-II is robotically filled with photo-polymerizable hydrogel, or any other material capable of acting as a supportive scaffold. The VBC-II is also filled with encapsulated dedifferentiation, differentiation, and growth factors to be attached as peptides, by lasers, to the polymerized hydrogel or released freely as chemotaxis factors, attracting pluripotent adult stem cells into the degenerating container of polymerized hydrogel by both holographic and multi photon lasers robotically controlled by the bio-CAD blueprint. Once completed, a porous formfitting cover is applied to help, where necessary, with the incubation process of tissues including, but not limited to: skin and other exposed tissues or organs when needed for healing process.

Making the Production Chamber

A production or inversion chamber 100 may be used to aid in the function of the first configuration of the vascular bed chamber (VBC-I) 10, as shown in FIG. 5. The production chamber 100 may be any shape or size as long as it encompasses the entirety of the VBC-I 10. Ideally, the production chamber 100 will be square or rectangular in shape and made from a transparent material, so that the user may easily see the production as it progresses. The base of the production chamber must have a square, transparent section in the middle 130, so that the lasers and microscopes may pass through to the production area of the VBC-I 10. The outer portion of the base 122 may be thermal regulated and a tight seal 132 made between the outer thermal regulated portion 122 of the base and the transparent middle section 130 of the base. The chamber 100 is designed so that VBC-I 10 is placed upside down within the chamber 100. The widest portion, the top of VBC-I 12, will be at the bottom 122 and the telescoping sides 14-20 will be raised in an inverse conical shape, as the base of VBC-I 22 is raised by clamps 108 attached to the support rod 102 in the production chamber 100. The chamber 100 may have spring loaded clamps 110 on the base 122 that allow the lip of the VBC-I 10 to attach and be stabilized to the base 122 of the production chamber 100.

Additionally, the production chamber 100 has a support rod 102 that runs the length of the chamber and is adjustable in the vertical plane. The rod 102 is attached to an adjustable slider 112 on the sides of the production chamber 100. The adjustable slider 112 is allowed to slide because of a sleeve support 104 on the side of the chamber 100, and a motorized knob 120 allowing the chamber 100 to be completely enclosed at all times. Attached to the rod 102 are clamps 108 that are adjustable along the length of the rod 102, to accommodate the various sizes in which the VBC110 can be made. A clear illustration of the relationship between the upper clamps 108 and their attachment to the support rod 102 by way of an adjustable slider 106 is shown in FIG. 4. The upper clamps 108 are supported by an adjustable slider 106 attached to the support rod 102 to allow the clamps 108 to slide in the horizontal plane, thus accommodating any base 22 size of VBC-I 10. The rod 102 is attached to a sleeve 104 that allows it to move up and down within the chamber 100; however, any method of raising or lowering can be used. The rod 102 is lowered down to the inverted base 22 of the VBC-I 10, and the clamps 108 along the rod 102 can be held in place by adjustable/motorized knobs 120. During production, a motorized knob 120 allows the rod 102 to move vertically up, thus raising the telescoping sides 14-20 of the VBC-I 10 to raise as the tissue or organ grows larger so that the tissue or organ is completely enclosed in the VBC-I 10.

The production chamber 100 should have at least as many input ports 114 as the corresponding VBC-I 10 being used with it. Ideally, the production chamber will have at least three input/output ports 114, 116, 124, 126, 128, where 128 is an example of an optional placement or additional placement port. These ports 114, 116, 124, 126, 128 allow for the exchange and flow of materials into and out of the chamber, continuing into the VBC-I 10, during and after production to aid in keeping the tissue or organ viable for transplantation or research. These ports 114, 116, 124, 126, 128 are designed to connect into the VBC-I 10, while it is in an inverted state.

Making VBC-I

The Vascular Bed Chamber-I (VBC-I) 10 is a receptacle that is telescopically increased in its height, robotically, to match the three-dimensional bio-fabrication process of tissue structures. This is done while simultaneously providing for the exchange of liquid mediums and materials within the fabricated structure and in the areas surrounding the tissue structure's production. It does this while providing for the tissue's support and maturation during the bio-fabrication process. It can also assist in regulating the buoyance of structural materials added to the VBC-I 10 by allowing changing of fluids of variable viscosities, supplied to the production area by peripheral devices, computer regulated and prearranged by the tissue's Bio-blueprint.

The VCB-I 10 device is made from cost effective materials and can me made of anything from biodegradable glucose polymers, protein polymers, glass or plastics, to stainless steel. Its parts can be produced separately by traditional casting, machining, drilling, molding and shaping means and assembled as described below, or three-dimensionally fabricated from a CAD model.

Its structure may be transparent, to allow during the tissue structures maturation phase, the laser manipulation of chemicals, materials and cells, robotically placed within the chamber during the structure's initial fabrication processes, or being supplied to the bio-fabrication site during tissues maturation phase through the VBC-I's entry ports 24a, 26a, 28b; or may be opaque to prefer light from affect the bio-fabrication of the maturing tissue structures.

FIG. 1 shows a cross section of VBC-I 10, upright and in its expanded state. This figure shows the interior and how the inflow and outflow tubes 24, 26, 28 are constructed and function within the VBC-I 10. The walls of the VBC-I 10 are constructed of tapered sections 14-20 that move along each other telescopically in height as the top section is lifted during the initial production phase. The diameter of distance across the top pf each section, ideally, is 2 mm larger than the section following below its position. The diameter of distance across the bottom of each section, ideally, is 4 mm smaller than its top opening. Except for the top and bottom sections, the wall of each section, ideally, is 9 mm in height and tapered to meet the 4 mm difference in diameter between its upper and lower openings.

The very top section, ideally, is 3 mm taller than the middle sections to provide for protruding lipped structure 12 used to catch hold of clamps 110 that hold it in place for its vertical lifting. Two clamps 108 for lifting are constructed with inner facing surfaces shaped to the contour of the wall of the VBC-I's base 22.

Figure 2:
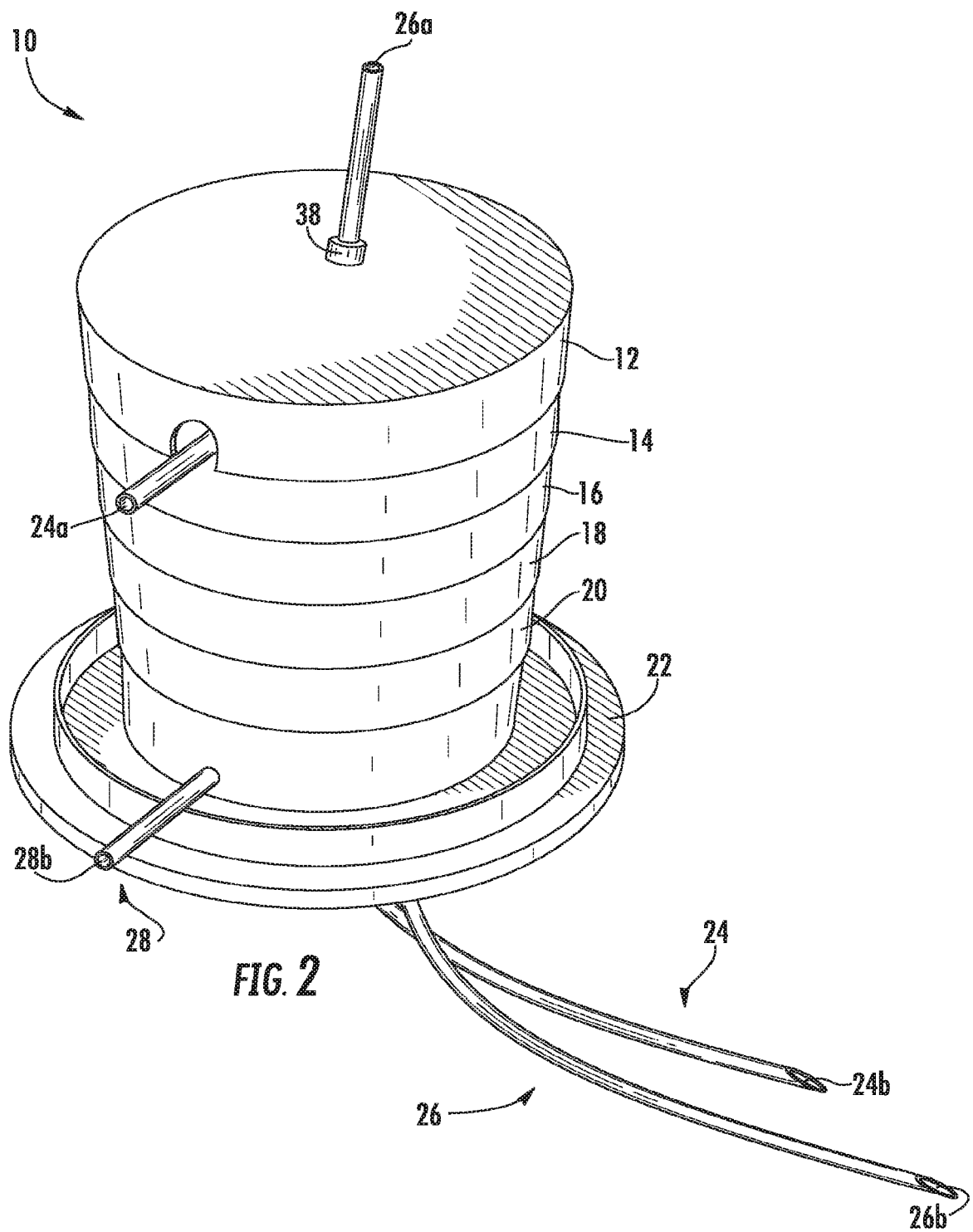
FIG. 2 illustrates a perspective view of the first embodiment of the apparatus in an expanded position for supporting the creation of tissues or organs outside of the body.
Figure 3:
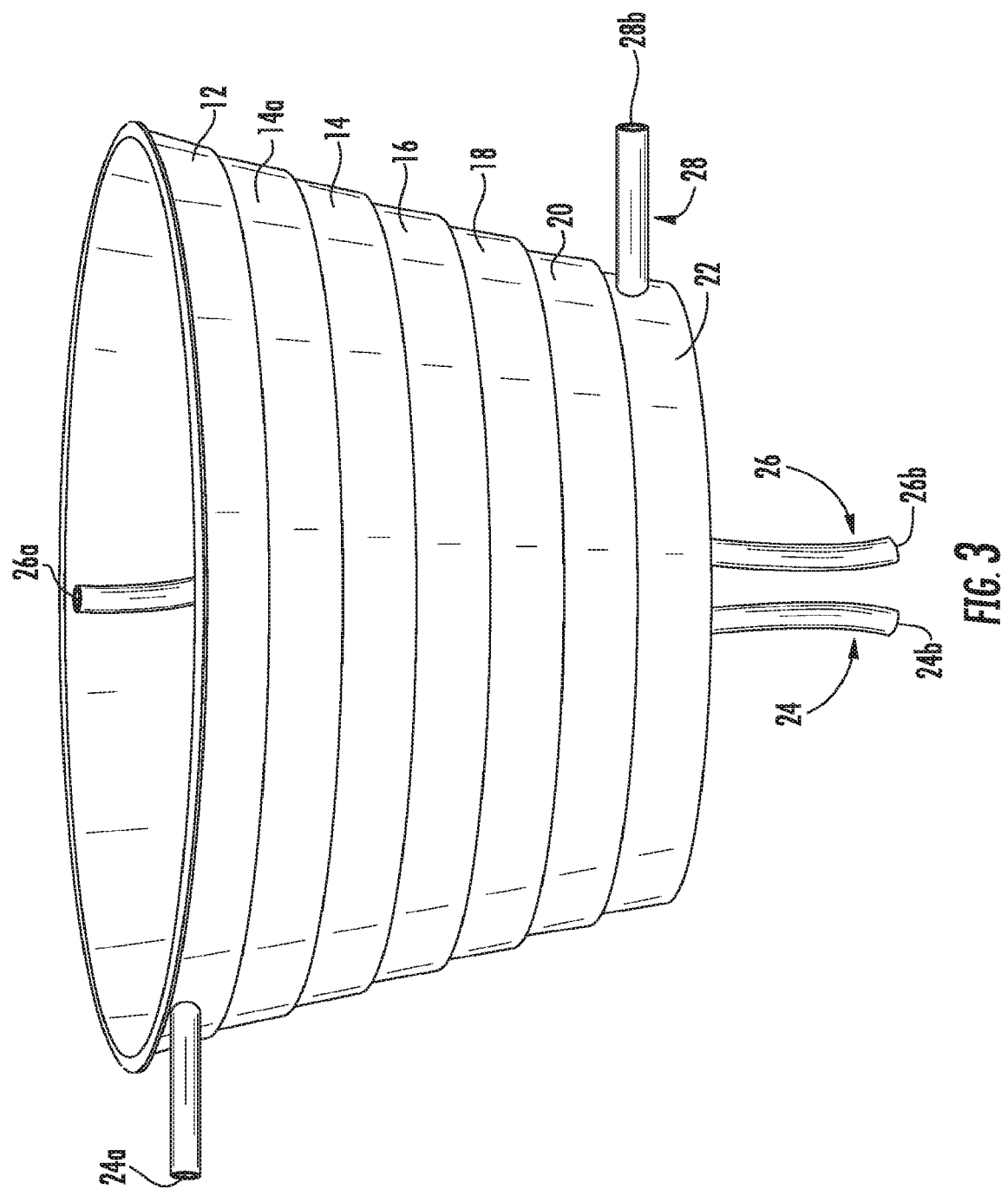
FIG. 3 illustrates a perspective view of the first embodiment of the apparatus in an expanded position, without the cover, to aid in expansion for supporting the creation of tissues or organs outside the body.

The top section lip 12 also provides for the snug fit of a cap for VBC-I 10, which can be applied when the initial fabrications stages are complete at the tissue's maturation stage, when it required. The cap affixed to the top section 12 has an entry port 26a in its top for a tube that connects to the bio-fabricating tissue's main input/output vessel, as illustrated in FIG. 2. The tube 26a may have adjustable sliding clamps/locking spacers 38 on both sides of the cap that allow modifiable depths of the tube's descent into the VBC-I 10.

The very top section also has an input port 24a with an outflow tube 28 that enters at an angle parallel to the VBC-I's base 22. The tubes' 24a, 28 openings are manufactured to fit flush with this section's inner wall, allowing its smooth telescopic movement across the outer wall of the lower connecting section. This port 28 allows for bottom up extraction/out flow of contents surrounding the bio-fabricating tissue structures.

The wall of the bottom section 20 is cupped with an inner depth of 7 mm, ideally, and an outer height of 9 mm, ideally. The bottom section 20 is attached to an appropriate base 22 at the time of the VBC-I's 10 assembly. The attachment of the base 22, done after all of the tapered walled sections 14-20 are placed in the order of their width, within each other, hold all the sections in place. In order to achieve this, the base 22 must at least be 4 mm wider that the lower opening of the top section 12. The bottom of the base 22 is shaped to match the specimen mounting mechanism centrally located on the robotic production stage.

Ideally, the base 22 may have a wall with an inner depth of 7 mm. The base may have two inlet tubes 24b, 26b that enter the VBC-I 10 perpendicular from the bottom and one outlet tube 28a that enters at a right angle from the side. The side outlet tube transverses the wall of VBC-I's base 22 and enters the wall of the VBC-I 10 within a few millimeters of its bottom 22. The side tube protrudes slightly into 28b VBC-I's 10 open area, allowing a regulated, top down extraction/out flow of contents surrounding the bio-fabricating tissue structures.

FIG. 6 illustrates the VBC-I 10 in an upside down, expanded state—the arrangement it would be in after production initially finishes. The two bottom ports 24b, 26b have attached tubes which enter at a right angle to the floor 22 of the VBC-I 10. These tubes 24b, 26b may be curved for convenience as they extend away from their entry points, allowing their clearance of the robotic production stage from a suspended position in its specimen mounting mechanism. One tube 26 is centrally located and protrudes about 5 mm, ideally, into the open area of the VBC-I 10. This tube is used for the variable supply of production, maintenance and regulatory fluids, materials and cells, to the fabrication sites (interior end of 26b) within the tissues by way of a main inlet blood vessel, fabricated from materials attached to tube's outer wall interior end of 26b during the initial bio-fabrication of the desired tissue structures. The second tube 28 meets flush with the bottom floor of the VBC-I 10. Its entry point is off to the side allowing a variable and independent flow of fluids and material discussed above, for the purposes disused above, form outward positions into the bio-fabrication sites.

Making VBC-2

Figure 7:
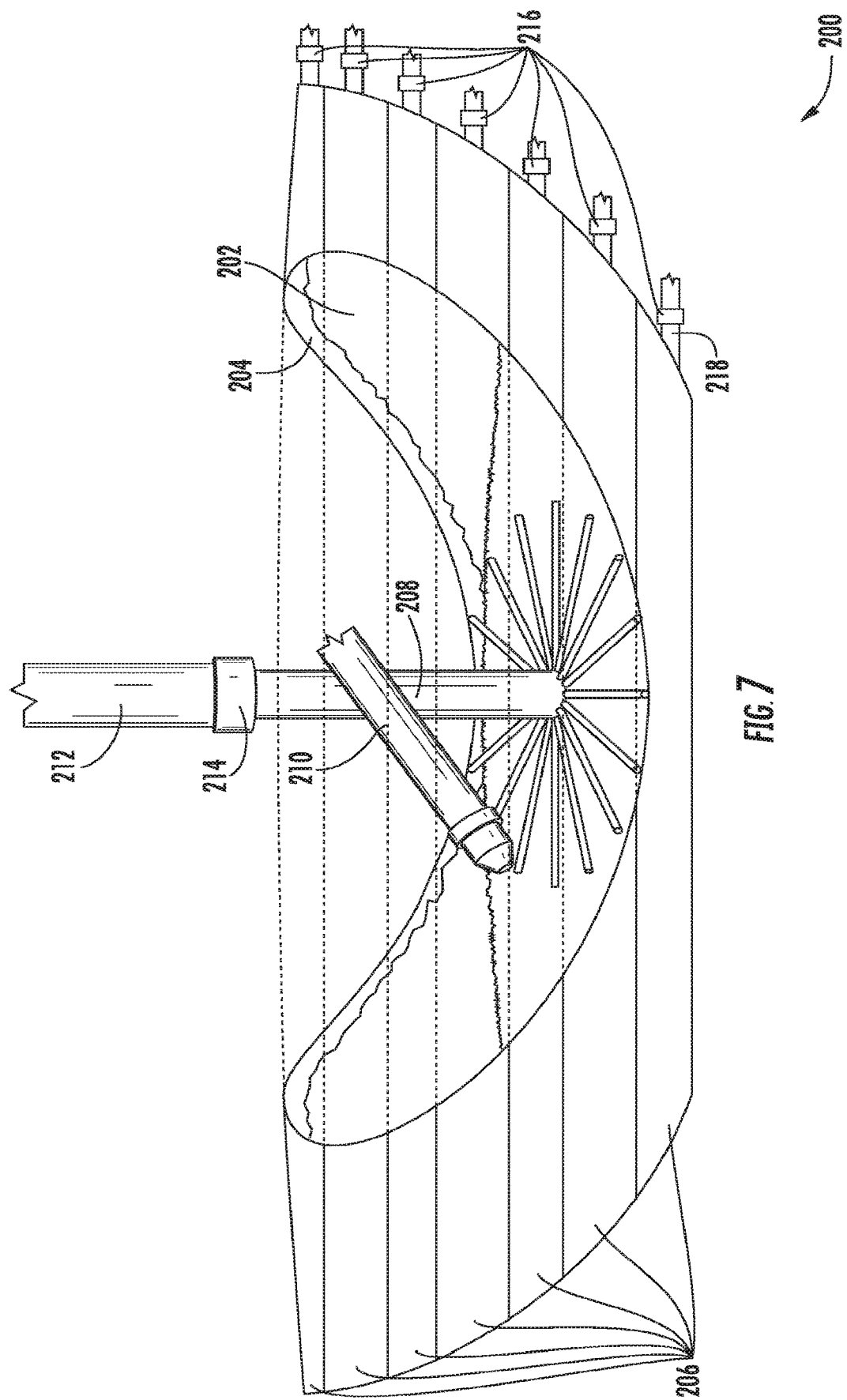
FIG. 7 illustrates a perspective view of the second embodiment placed directly on an open wound for the direct repair of tissues or organs on a human body.

A second configuration of the vascular bed chamber (hereinafter referenced as VBC-II) 200 is intended for tissue, organ, or complete limb regeneration directly on a patient's body/wound 202. FIG. 7 illustrates a complete setup of the VBC-II in a state ready for production of a new tissue or organ. The VBC-II 200 is a fitted chamber, produced specifically to fit the patient and the tissue/organ/limb 202 to be regenerated. The chamber 200 serves as an interface with the patient's body's regenerative activities, the bio-stimulatory scaffold described above, and the ex vivo robotically controlled systems. The chamber 200 is needed to aid in the stimulation and support of the regenerative processes designed in the method. The chamber 200 coordinates the interface of computer aided manufacturing, bio-stimulatory and tissue regeneration through the chroma code, incorporated into the selected blueprint.

Figure 10:
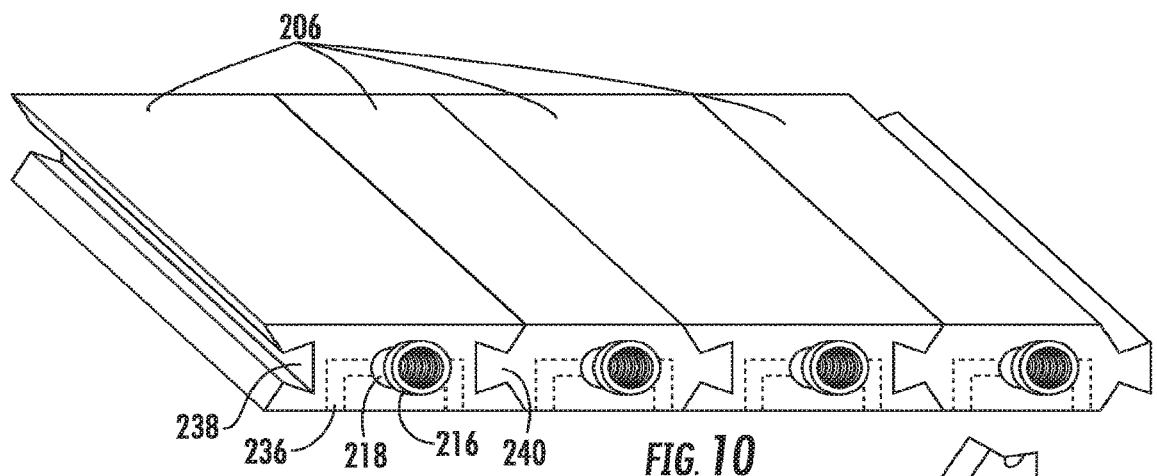
FIG. 10 illustrates the interlocking sections that make up the second embodiment with inflow channels and outflow ports shown, for tissue or organ repair directly on the human body.
Figure 11:
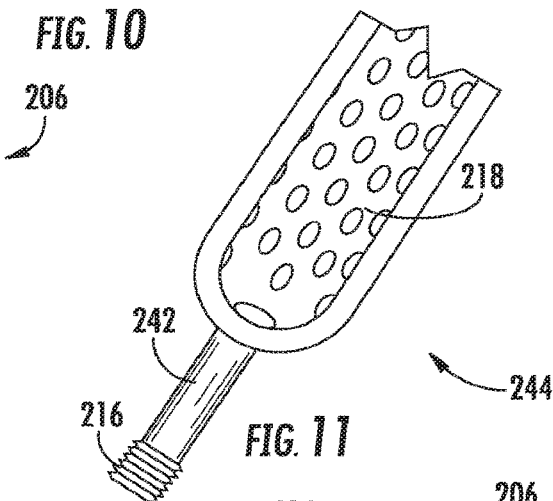
FIG. 11 illustrates a sectional view of an embodiment for the repair of digits to be attached to the second embodiment for repair of tissues or organs directly on the human body.
Figure 12:
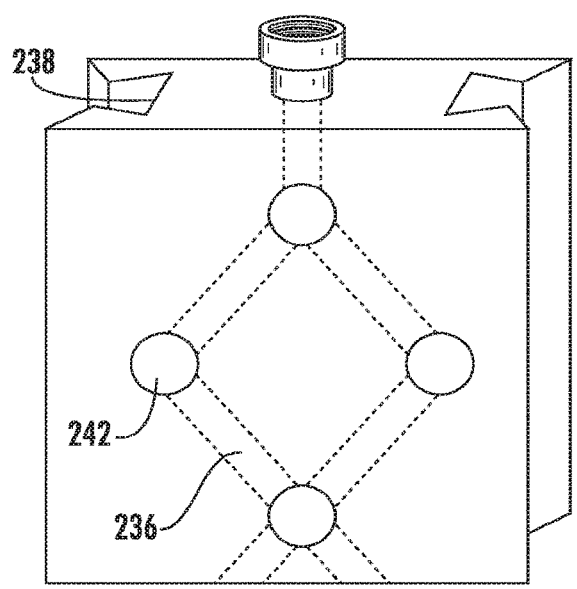
FIG. 12 illustrates a bottom view of a section comprising the second embodiment with inflow ports and channels shown, as well as the outflow port shown at the top of the figure, for tissue or organ repair directly on the human body.
Figure 13:
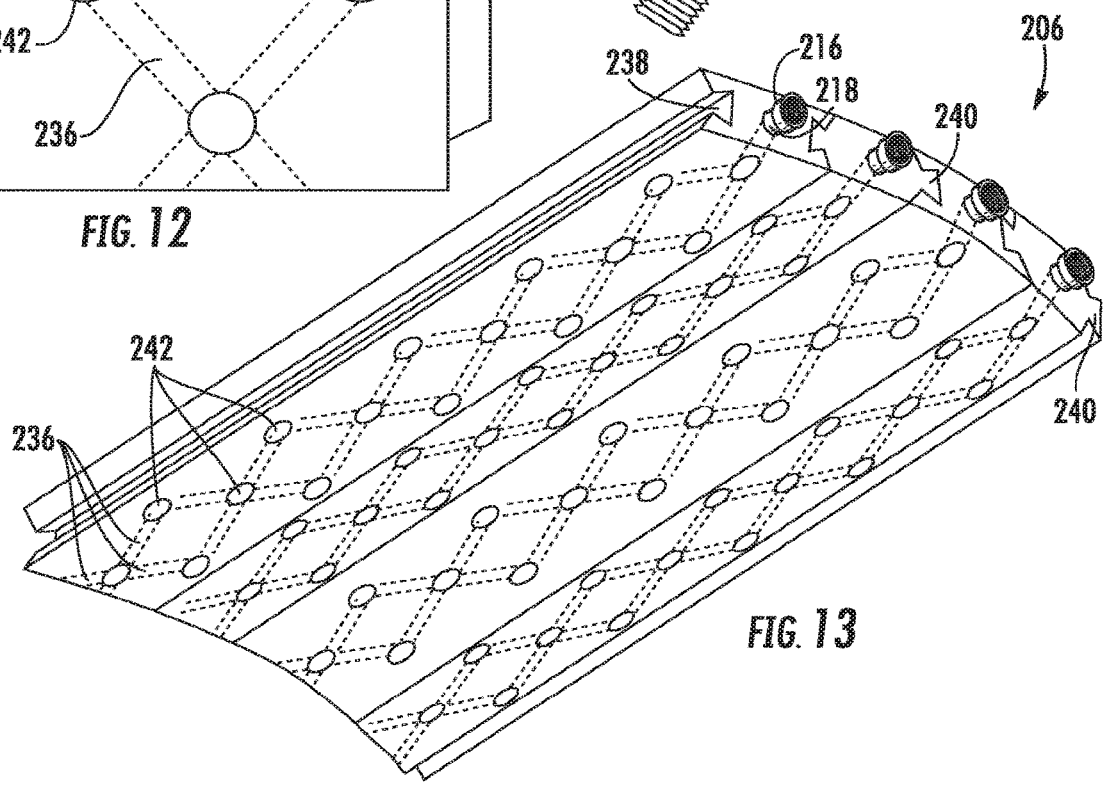
FIG. 13 illustrates a bottom view of several sections that comprise the second embodiment with inflow channels and ports shown, as well as the outflow ports, for tissue or organ repair directly on the human body.

The chamber of the VBC-II 200 is designed for construction in individual segments 206 that may be transparent in nature. Segmenting the chamber allows the user to customize the size and shape to fit the biofabrication site and tissue structure requirements for patient specific needs. The segments interlock along the sides 238, 240, alternating male and female connectors, as shown in FIG. 10. FIGS. 12 and 13 illustrate the underside of each segment being lined with inflow holes 242 that lead to channels 236 within the segments 206 to allow for recirculation and extraction of fluids and materials that aid in regeneration. At the end of each segment 206 are outflow ports 218 to aid in the recirculation of fluids and materials through the chamber. These ports 218 should have a threaded end 216 to allow for the attachment of additional segments 206 or accessory attachments, such as a small chamber for the regeneration of digits 244. FIG. 14 illustrates this digit attachment 244 having one inflow port 242 that attaches to a single segment 206 by way of the interlocking, preferably screw, ends 216. Inside of the digit attachment chamber are holes 218 that allow for the outflow and recirculation of fluids and other biological materials.

To use VBC-II 200 with the method described above, the user must create a blastemal-inducing film 204. This can be created using a waxy paper 224, laying down a fatty acid mixture containing integrins 222 and overlaying the mixture with a protective hydrophilic gauze 220, as shown in FIG. 8. This creates two regions, a hydrophilic region 228 and a hydrophobic region 230 separated into their own compartments 226. This film 204 must be molded to fit over the patient's wound 202 area in order to begin the regenerative process. The best way is to heat the film 204 over a mold 232 having been created to fit the patient's wound 202, the mold illustrated in FIG. 9. FIG. 9 illustrates the mold 232 of the wound 202 with the blastemal film 204 overlaying it. The mold 232 is then heated, preferably from an internal heating component 234, but may be done with any heating method. The heat allows the film 204 to fit the mold 232 of the wound 202 so that it will fit securely over the wound 202 directly on the patient's body.

Once the film 204 has been created and inserted on or inside of the patient's body in the area to be regenerated, the segments 206 can be attached together and overlay the area to be regenerated. Next, a tube is inserted perpendicular to the film. This tube will be the fabrication site, where the cells are placed to regenerate the affected area on the patient. FIG. 14 shows the tube comprised of several sections. At the very end of the tube, where it meets the film 204, are tubules 246 that layover the blastema film 204. The tube may expand telescopically, one section 212 being slightly larger than the other 208, allowing the tube to collapse down for easy and damage-free removal. FIG. 15 illustrates the tube in its collapsed state. The tubules 246 may be drawn up the sides of the small half of the tube 208, the bottom half. Then the top half of the tube 212, preferably having a lip 214, will slide over the bottom half 208 and the tubules 246, completely encasing them so that a singular tube is removed from the site once regeneration is complete. The tube allows for the inflow, through the top section 212 down to the bottom section 208 and finally through the tubules 246, of materials and disperses the materials through the outflow ports 248 located on each tubule 246.

Figure 16:
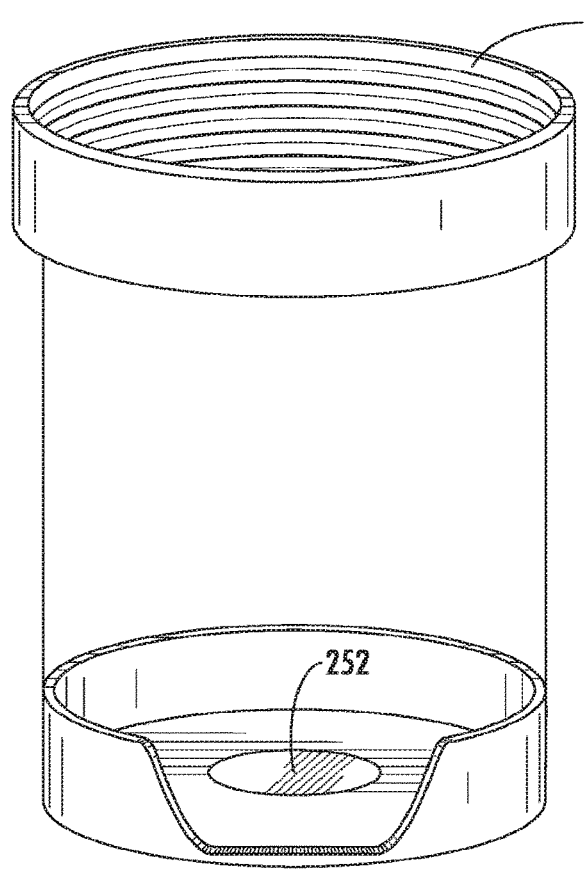
FIG. 16 illustrates the laser fabrication goggle, with a transparent opening at the bottom, which houses the microscope objective lens during the repair of tissue or organs directly on the human body.
Figure 17:
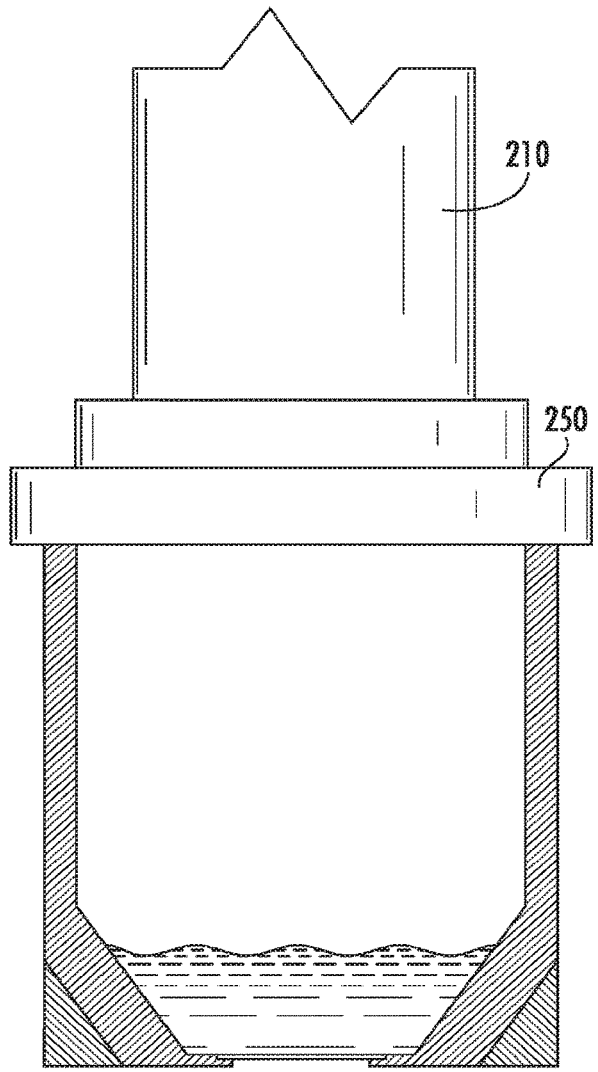
FIG. 17 illustrates the microscope objective lens in the goggle with immersion oil to aid in repair of tissue or organs directly on the human body.
Figure 18:
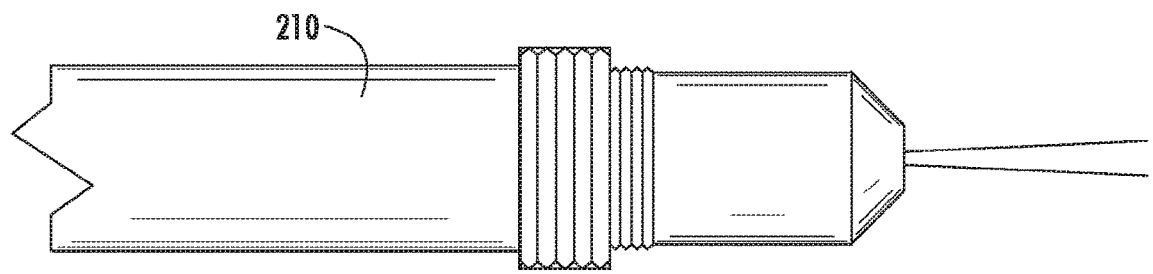
FIG. 18 illustrates the completed form of the laser fabrication goggle, including the microscope objective lens, that will aid in repair of tissue or organs directly on the human body.
Figure 19A:
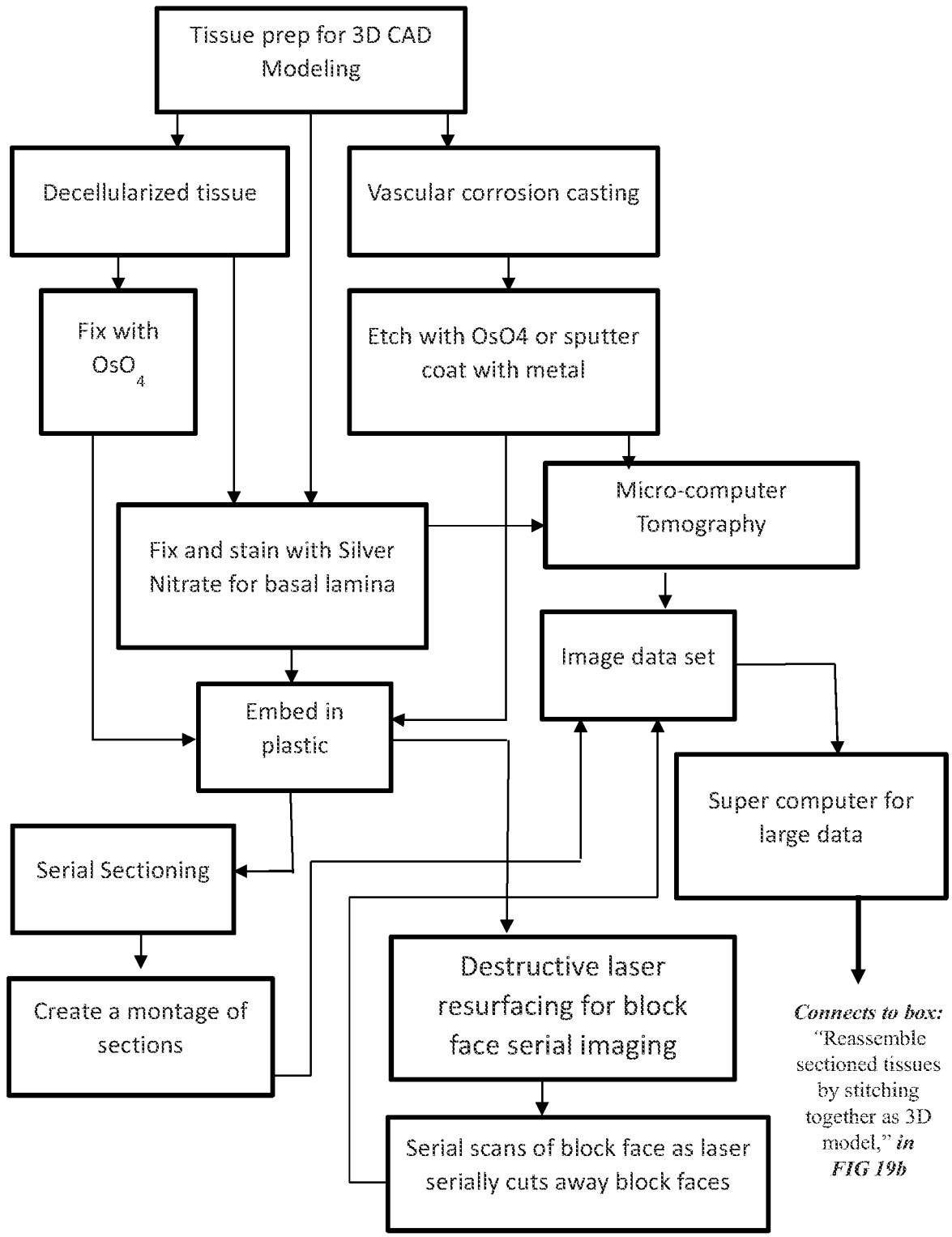
FIG. 19A Capturing Tissue's authentic 3-D Architecture, FIG. 19B Designing and Chroma Coding Bio-CAD Blueprint, FIG. 19C Coding the Environmental Factors for Bio-CAD Blueprint, FIG. 19D Regulation of environmental conditions within the Vascular Bed Chamber; illustrates a flow chart of the method from the beginning stage of which tissue to regenerate, through the computer modeling and tissue preparation, all the way to the finished product either on/in the patient's body, or ready for transplantation.
Figure 19B:
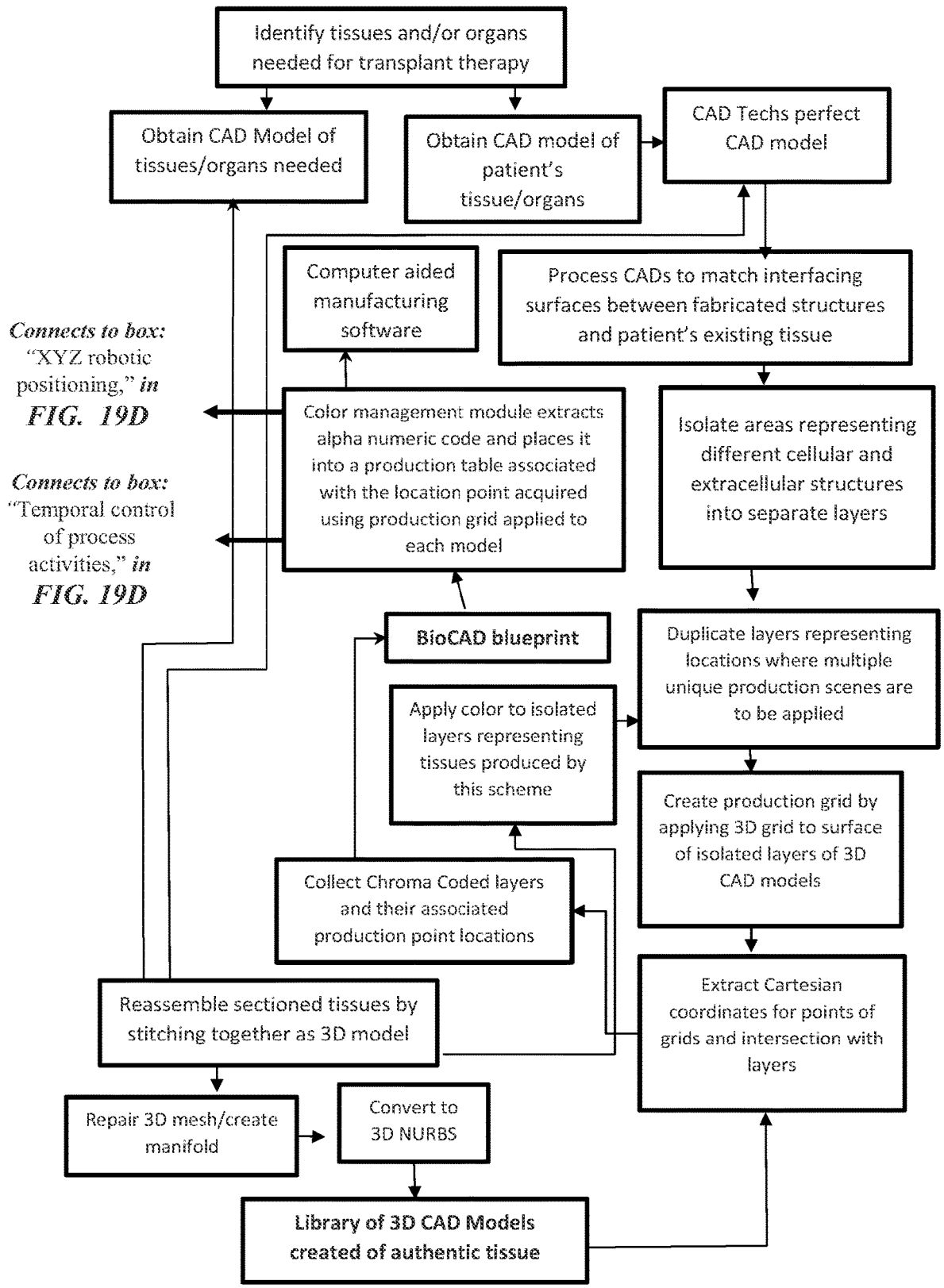
Figure 19C:
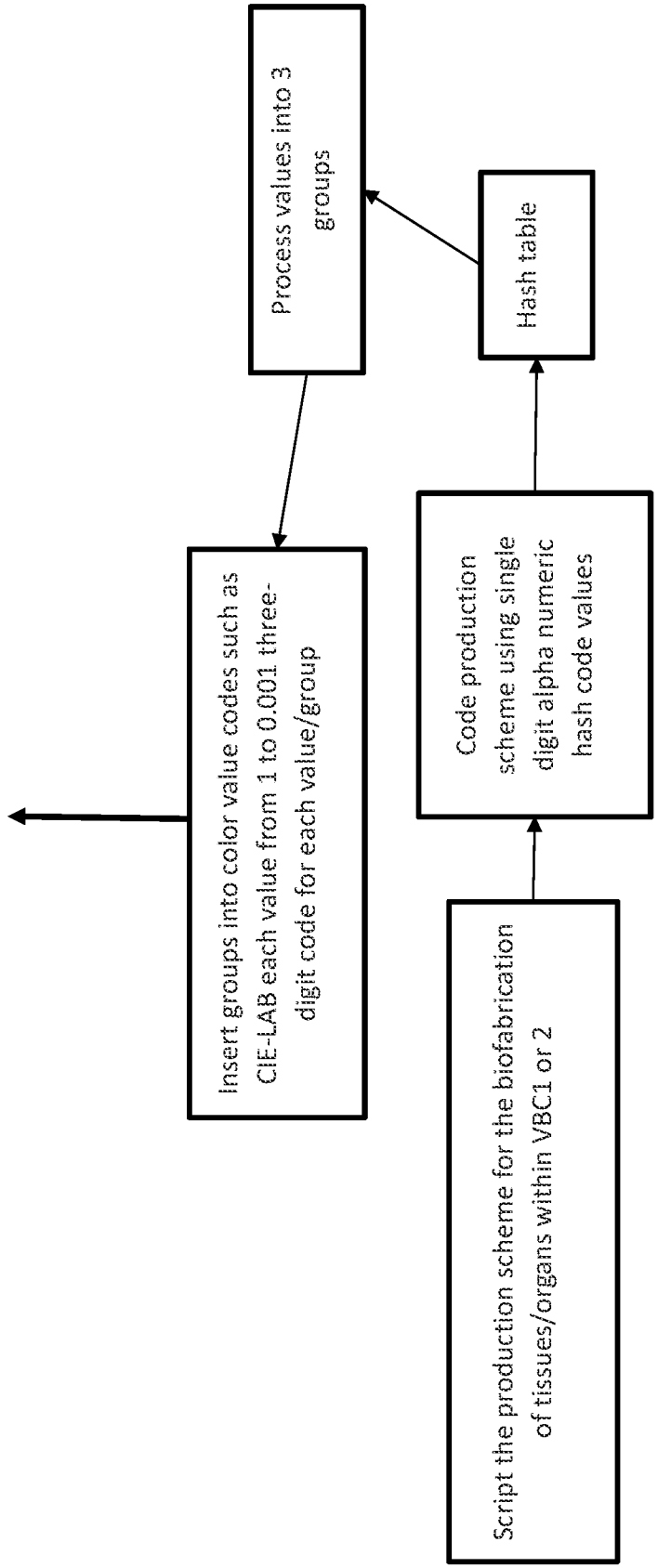
Figure 19D:
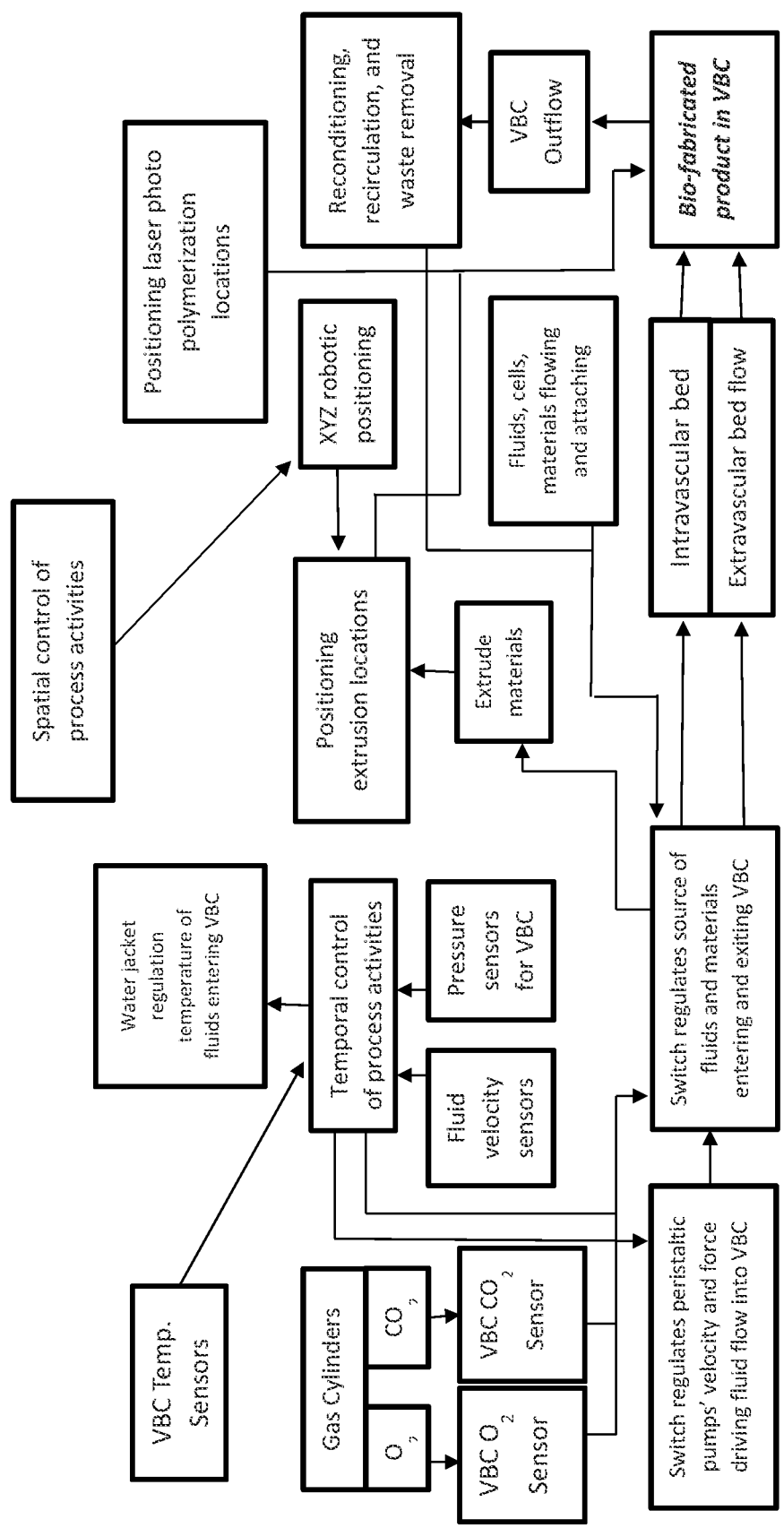

Finally, the laser 210 that will aid in production will be placed. Ideally, it is used at a 45 degree angle to the inflow tube that serves as the fabrication site, as illustrated in FIG. 7. FIGS. 16 and 17 illustrate the laser fabrication goggle 254 that will be fitted over the laser 210. This is a rounded chamber designed to fit over the microscope objective lens end of the laser 210. The goggle 254 should have female threads at the top 250 to allow it to screw onto the laser. Additionally, the bottom of the chamber should have at least a transparent section in the middle 252 that will allow the light from the laser to pass through. FIG. 17 illustrates the entire assembly, with the laser 210 in the goggle 254, having been screwed into the top 250, with the laser sitting in immersion oil. Once the laser 210 has been placed, VBC-II 200 is considered to be completely assembled, and fabrication/regeneration can begin.

What is claimed is:

1. An apparatus comprising a culture chamber keeping artificially created tissues alive; a receptacle that is telescopically increased in its height, robotically, to match the three-dimensional bio-fabrication process of tissue structures or bio-stimulatory scaffold; and the ex vivo robotically controlled systems that aid by stimulating and supporting of the regenerative processes; the diameter of distance across the top of each section, ideally, is 2 mm larger than the section following below its position; the diameter of distance across the bottom of each section, ideally, is 4 mm smaller than its top opening; except for the top and bottom sections, the wall of each section, ideally, is 9 mm in height and tapered to meet the 4 mm difference in diameter between its upper and lower openings; the very top section, ideally, is 3 mm taller than the middle sections to provide for protruding lipped structure used to catch hold of clamps that hold it in place for its vertical lifting; two clamps for lifting are constructed with inner facing surfaces shaped to the contour of the wall of the culture chamber's base the top section lip also provides for the snug fit of a cap for culture chamber, which can be applied when the initial fabrications stages are complete at the tissue's maturation stage, the cap affixed to the top section has an entry port in its top for a tube that connects to the bio-fabricating tissue's main input/output vessel, the tube may have adjustable sliding clamps/locking spacers on both sides of the cap that allow modifiable depths of the tube's descent into the culture chamber; the very top section also has an input port with an outflow tube that enters at an angle parallel to the culture chamber's base, the tubes' openings are manufactured to fit flush with this section's inner wall, allowing its smooth telescopic movement across the outer wall of the lower connecting section, this port allows for bottom up extraction/out flow of contents surrounding the bio-fabricating tissue structures; the wall of the bottom section is cupped with an inner depth of 7 mm, ideally, and an outer height of 9 mm, ideally; the bottom section is attached to an appropriate base at the time of the culture chamber's assembly; the attachment of the base, done after all of the tapered walled sections are placed in the order of their width, within each other, hold all the sections in place; the base must at least be 4 mm wider that the lower opening of the top section; the bottom of the base is shaped to match the specimen mounting mechanism centrally located on the robotic production stage; the base may have a wall with an inner depth of 7 mm; the base may have two inlet tubes that enter the culture chamber perpendicular from the bottom and one outlet tube that enters at a right angle from the side. The side outlet tube transverses the wall of culture chamber's base and enters the wall of the culture chamber within a few millimeters of its bottom; the side tube protrudes slightly into culture chamber's open area, allowing a regulated, top-down extraction/out flow of contents surrounding the bio-fabricating tissue structures; made from cost effective materials anything from biodegradable glucose polymers, protein polymers, glass or plastics, to stainless steel, may be transparent, to allow during the tissue structures maturation phase, the laser manipulation of chemicals, materials and cells, robotically placed within the culture chamber during the structure's initial fabrication processes, or being supplied to the bio-fabrication site during tissues maturation phase through entry ports; or opaque to prefer light's effect on the bio-fabrication of the maturing tissue structures; culture chamber upright and in its expanded state the interior interfaces the inflow and outflow tubes are constructed and function within the culture chamber, done while simultaneously providing for the exchange of liquid mediums and materials within the fabricated structure and in the areas surrounding the tissue structure's production; culture chamber does this while providing for the tissue's support and maturation during the bio-fabrication process, also assisting in regulation of the buoyance of structural materials added to the culture chamber by allowing changing of fluids of variable viscosities, supplied to the production area by peripheral devices, computer regulated and prearranged by the tissue's Bio-blueprint.

2. An apparatus comprising a production chamber shape to encompasses the entirety of the culture chamber in an upside down, expanded state—the two bottom ports attached tubes enter at a right angle to the floor of the culture chamber in an upside down, expanded state, tubes may be curved for convenience as they extend away from their entry points, allowing their clearance of the robotic production stage from a suspended position in its specimen mounting mechanism; one tube is centrally located and protrudes about 5 mm, ideally, into the open area of the culture chamber in an upside down, expanded state; this tube is used for the variable supply of production, maintenance and regulatory fluids, materials and cells, to the fabrication sites within the tissues by way of a main inlet blood vessel, fabricated from materials attached to tube's outer wall during the initial bio-fabrication of the desired tissue structures. The second tube meets flush with the bottom floor of the culture chamber in an upside down, expanded state; entry point off to the side allowing a variable and independent flow of fluids and material from outward positions into the bio-fabrication sites; ideally, made of transparent material, base must have a square, transparent section in the middle, allowing lasers to accurately pass through to the production area of the culture chamber; outer portion of the base may be thermal regulated and a tight seal made between the outer thermal regulated portion of the base and the transparent middle section of the base; culture chamber is placed upside down within the production chamber, widest portion, the top of culture chamber, at the bottom, the telescoping sides raised in an inverse conical shape, the base is raised by clamps attached to the support rod in the production chamber having spring loaded clamps on the base that allow the lip of the culture chamber to attach and be stabilized to the base of the production chamber having a support rod that runs the length of the chamber and is adjustable in the vertical plane, attached to an adjustable slider on the sides of the production chamber; allowed to slide because of a sleeve support on the side of the production chamber, and a motorized knob allowing the production chamber to be completely enclosed at all times; attached to the rod are clamps that are adjustable along the length of the rod, to accommodate the various sizes in which the culture chamber can be made, the relationship between the upper clamps and their attachment to the support rod by way of an adjustable slider; upper clamps supported by an adjustable slider attached to the support rod to allow the clamps to slide in the horizontal plane, accommodating any base size of culture chamber; rod is attached to a sleeve that allows it to move up and down within the production chamber; however, rod is lowered down to the inverted base of the culture chamber, and the clamps along the rod can be held in place by adjustable/motorized knobs allowing rod to move vertically up, thus raising the telescoping sides of the culture chamber to raise as the tissue or organ grows larger so that the tissue or organ is completely enclosed in the culture chamber; the production chamber should have at least as many input ports as the corresponding culture chamber being used with it, the production chamber will have at least three input/output ports where port allow for the exchange and flow of materials into and out of the chamber, continuing into the culture chamber, during and after production, to aid in keeping the tissue or organ viable for transplantation or research; ports are designed to connect into the culture chamber while it is in an inverted state.

3. Apparatus of claim 1 or 2 further constructed in a combined configuration for tissue, organ, or complete limb regeneration directly on a patient's body/wound; comprising a fitted production/culture chamber, produced specifically to fit a patient and their tissue/organ/limb to be regenerated; as an interface with the patient's body's regenerative activities; constructed of individual segments, allowing customization of its size and shape to fit the bio fabrication site and tissue structure's requirements; interlock along the sides, alternating male and female connectors; underside of each segment being lined with inflow holes that lead to channels within the segments to allow for recirculation and extraction of fluids and materials that aid in regeneration, at the end of each segment are outflow ports that aid the recirculation of fluids and materials through the chamber; ports should have a threaded end to allow for the attachment of additional segments or accessory attachments such as a small chamber for the regeneration of digits having one inflow port that attaches to a single segment by way of the interlocking, preferably screw, ends; inside of the digit attachment chamber are holes that allow for the outflow and recirculation of fluids and other biological materials.

4. The apparatus of claim 3 one side further comprising a blastemal-inducing film to be inserted on or inside of the patient's body in the area to be regenerated, created using a waxy paper, laying down a fatty acid mixture containing integrins and overlaying the mixture with a protective hydrophilic gauze, creating two regions, a hydrophilic region and a hydrophobic region separated into their own compartments; molded to fit over the patient's wound by heating over a mold created to fit the patient's wound, so that it will fit securely over the wound directly on the patient's body; the segments can be attached together and overlay the area to be regenerated.

5. The apparatus of claim 3 further comprising, a tube is inserted perpendicular to the blastema-induction film within the fabrication site; tube allows for the inflow, through the top section down to the bottom section and finally through the tubules; the tube comprised of several sections, the very end of the tube; where it meets the film, are tubules layover the blastema film where materials and cells are disperses through the outflow ports located on each tubule expand telescopically, one section being slightly larger than the other, allowing the tube to collapse down for easy and damage-free removal; tubules are drawn up the sides of the small half of the tube, the bottom half; the top half of the tube, preferably having a lip, will slide over the bottom half and the tubules, completely encasing them so that a singular tube is removed from the site once regeneration is complete.

6. The apparatus of claim 3 further comprising an ex vivo robotically controlled laser for in situ production of bio-stimulatory scaffold to aid by stimulating and supporting of the regenerative processes, placed, at a 45 degree angle to the inflow tube that serves as the fabrication site; uses laser fabrication goggle fitted over the laser; a rounded chamber designed to fit over a microscope objective lens end of the laser; goggle should have female threads at the top to allow it to screw onto the laser; bottom of the chamber should have at least a transparent section in the middle that will allow the light from the laser to pass through the entire assembly, with the laser in the goggle, having been screwed into the top, with the laser microscope objective lens sitting in immersion oil to correct light's diffraction angles as they pass through the transparent section in the middle of goggle and enter the medium where photopolymerization occurs at robotically positioned coordinates producing a bio-stimulatory scaffold, a chromatically coded blueprint interfacing the computer aided manufacturing and tissue regeneration using structural elements that are wearable or standalone; consisting of boundaries in the former which can be telescopic or the later which can be modularly applied to fit the contours of the needed tissue structures with, at least one entry and exit port that allows the circulation of fluids and biological materials, with custom dimensions designed to a patient's specific tissue needs, dimensions that create a volumetric space of the size, and shape needed to enclose the required regions of a tissues' authentic septal architecture, containing authentic vascular architecture, whose chamber's dimensions provide a framework for supporting both the in situ and the in vitro creation of organ specific functional tissues in their authentic micro and macro architectures, contains sensors that generate and feed data back to computer capable of regulating dispensing of molecular and environmental factors that control cell behaviors etc. and the conditions in a bio reactive environment.

* * * * *